(12) United States Patent
Hanai et al.

(10) Patent No.: US 6,639,057 B1
(45) Date of Patent: Oct. 28, 2003

(54) MONOCLONAL ANTIBODY AGAINST HUMAN TELOMERASE CATALYTIC SUBUNIT

(75) Inventors: Nobuo Hanai, Tokyo (JP); Motoo Yamasaki, Tokyo (JP); Kenji Shibata, Tokyo (JP); Akiko Furuya, Tokyo (JP); Osamu Mikuni, Kawasaki (JP); Hideharu Anazawa, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/424,226

(22) PCT Filed: Mar. 26, 1999

(86) PCT No.: PCT/JP99/01557

§ 371 (c)(1),
(2), (4) Date: Nov. 26, 1999

(87) PCT Pub. No.: WO99/50407

PCT Pub. Date: Oct. 7, 1999

(30) Foreign Application Priority Data

Mar. 26, 1998 (JP) .......................................... 10-098486

(51) Int. Cl.[7] .............................................. C07K 16/00
(52) U.S. Cl. .............................. 530/388.26; 530/387.3; 530/388.1; 530/388.15; 424/141.1; 424/142.1; 424/146.1; 435/325; 435/338
(58) Field of Search .......................... 530/387.1, 388.1, 530/387.3, 388.26, 388.15; 424/141.1, 142.1, 146.1; 436/813; 435/325, 338

(56) References Cited

U.S. PATENT DOCUMENTS 5,958,680 A    9/1999  Villeponteau et al.
6,166,178 A  * 12/2000  Cech et al. .................. 530/324

FOREIGN PATENT DOCUMENTS

| AU | 48036/97 | 5/1998 |
| AU | 48073/97 | 5/1998 |
| GB | 2 317 891 | 4/1998 |
| WO | WO 98/37181 | 8/1998 |

OTHER PUBLICATIONS

T.M. Nakamura et al., "Telomerase Cataltic Subunit Homologs from Fission Yeast and Human", Science, vol. 277, No. 5328, pp. 955–959, Aug. 15, 1997.

M. Meyerson et al.,Cell, vol. 90, No. 4, pp. 785–795, "hEST2, The Putative Human Telomerase Catalytic Subunit Gene, is Up–Regulated in Tumor Cells and During Immortalization",Aug. 22, 1997.

S. Ramakrishnan et al., "Characterization of Human Telomerase Complex", Proc. Natl. Acad. Sci USA, vol. 94, pp. 10075–10079, Sep. 1997.

* cited by examiner

*Primary Examiner*—Laurie Scheiner
(74) *Attorney, Agent, or Firm*—Oblon, Spivak, McClelland, Maier & Neustadt, P.C.

(57) ABSTRACT

The present invention provides a monoclonal antibody which can specifically and efficiently recognize hTERT protein; which is the catalytic subunit of telomerase, and provides a human chimeric antibody, a CDR grafted antibody, a single chain antibody, and a disulfide stabilized antibody each containing the monoclonal antibody. In addition, the present invention provides a method for detecting/quantitating hTERT protein using these antibodies, and provides diagnosis method, diagnosis agent, and therapeutic agent, for diseases, such as cancer, in which telomerase is involved using these bodies.

12 Claims, 10 Drawing Sheets

1  293 cell lysate
2  WI38 cell lysate $1 \times 10^5$ cells/lane

FIG.9
|  | 293 | WI38 |
|---|---|---|
| KM844 | 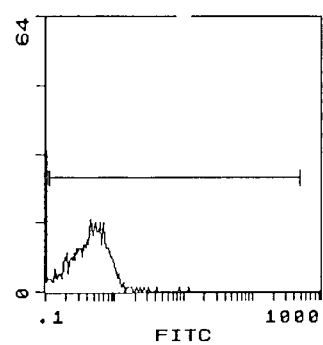 | 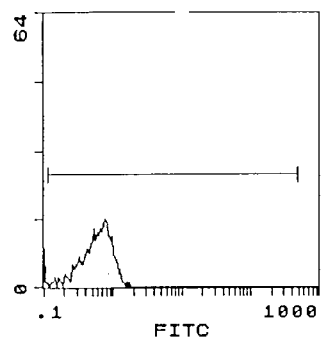 |
| KM2582 | 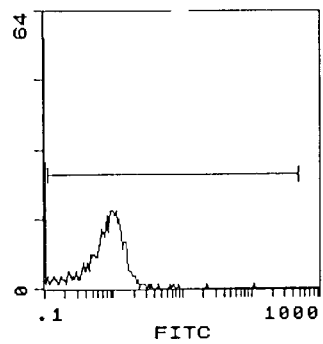 | 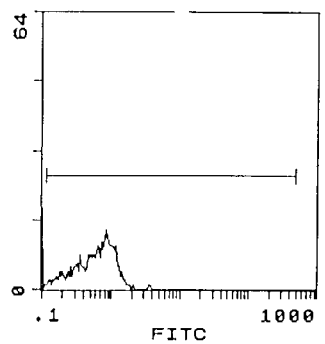 |
| KM2604 | 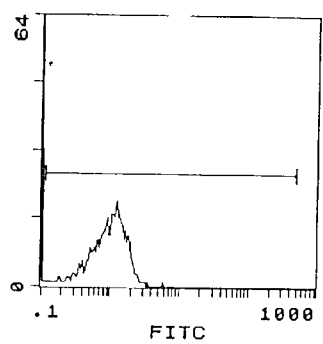 | 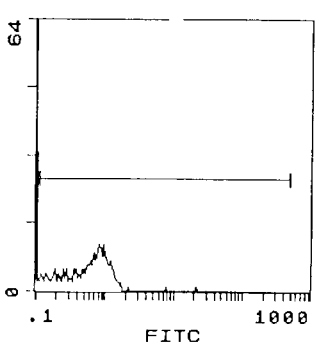 |

SEQUENCE LISTING

<160> NUMBER OF SEQ ID NOS: 6

<210> SEQ ID NO 1
<211> LENGTH: 17
<212> TYPE: PRT
<213> ORGANISM: Homo sapiens

<400> SEQUENCE: 1

Met Pro Arg Ala Pro Arg Ser Arg Ala Val Arg Ser Leu Leu Arg Ser
1               5                   10                  15

Cys

<210> SEQ ID NO 2
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = N-Acetyl-L-Alanine

<400> SEQUENCE: 2

Xaa Arg Thr Phe Arg Arg Glu Lys Arg Ala Glu Arg Leu Thr Ser Arg
1               5                   10                  15

Val Lys Ala Cys
            20

<210> SEQ ID NO 3
<211> LENGTH: 16
<212> TYPE: PRT
<213> ORGANISM: Homo sapiens

<400> SEQUENCE: 3

Cys Ala Ala Asn Pro Ala Leu Pro Ser Asp Phe Lys Thr Ile Leu Asp
1               5                   10                  15

<210> SEQ ID NO 4
<211> LENGTH: 30
<212> TYPE: DNA
<213> ORGANISM: Artificial Sequence
<220> FEATURE:
<223> OTHER INFORMATION: Synthetic DNA

<400> SEQUENCE: 4
ccggatccat gagtgtgtac gtcgtcgagc         30

<210> SEQ ID NO 5
<211> LENGTH: 34
<212> TYPE: DNA
<213> ORGANISM: Artificial Sequence
<220> FEATURE:
<223> OTHER INFORMATION: Synthetic DNA

<400> SEQUENCE: 5
gggaattctt agatcccctg gcactggacg tagg     34

<210> SEQ ID NO 6
<211> LENGTH: 283
<212> TYPE: PRT
<213> ORGANISM: Homo sapiens

<400> SEQUENCE: 6

Met Ser Val Tyr Val Val Glu Leu Leu Arg Ser Phe Phe Tyr Val Thr
1               5                   10                  15

Glu Thr Thr Phe Gln Lys Asn Arg Leu Phe Phe Tyr Arg Lys Ser Val
                20                  25                  30

Trp Ser Lys Leu Gln Ser Ile Gly Ile Arg Gln His Leu Lys Arg Val
            35                  40                  45

Gln Leu Arg Glu Leu Ser Glu Ala Glu Val Arg Gln His Arg Glu Ala
        50                  55                  60

Arg Pro Ala Leu Leu Thr Ser Arg Leu Arg Phe Ile Pro Lys Pro Asp
65                  70                  75                  80

Gly Leu Arg Pro Ile Val Asn Met Asp Tyr Val Val Gly Ala Arg Thr
                85                  90                  95

Phe Arg Arg Glu Lys Arg Ala Glu Arg Leu Thr Ser Arg Val Lys Ala
                100                 105                 110

Leu Phe Ser Val Leu Asn Tyr Glu Arg Ala Arg Arg Pro Gly Leu Leu
            115                 120                 125

Gly Ala Ser Val Leu Gly Leu Asp Asp Ile His Arg Ala Trp Arg Thr
        130                 135                 140

Phe Val Leu Arg Val Arg Ala Gln Asp Pro Pro Glu Leu Tyr Phe
145                 150                 155                 160

Val Lys Val Asp Val Thr Gly Ala Tyr Asp Thr Ile Pro Gln Asp Arg
                165                 170                 175

Leu Thr Glu Val Ile Ala Ser Ile Ile Lys Pro Gln Asn Thr Tyr Cys
            180                 185                 190

Val Arg Arg Tyr Ala Val Val Gln Lys Ala Ala His Gly His Val Arg
        195                 200                 205

Lys Ala Phe Lys Ser His Val Ser Thr Leu Thr Asp Leu Gln Pro Tyr
    210                 215                 220

```
-continued

Met Arg Gln Phe Val Ala His Leu Gln Glu Thr Ser Pro Leu Arg Asp
225             230             235             240

Ala Val Val Ile Glu Gln Ser Ser Ser Leu Asn Glu Ala Ser Ser Gly
            245             250             255

Leu Phe Asp Val Phe Leu Arg Phe Met Cys His His Ala Val Arg Ile
            260             265             270

Arg Gly Lys Ser Tyr Val Gln Cys Gln Gly Ile
            275             280
```

MONOCLONAL ANTIBODY AGAINST HUMAN TELOMERASE CATALYTIC SUBUNIT

TECHNICAL FIELD

The present invention relates to a monoclonal antibody which reacts specifically to human telomerase catalytic subunit (hereinafter referred to as hTERT). In addition, the present invention relates to a diagnosis method, diagnosis agent, and therapeutic agent using this monoclonal antibody for diseases in which telomerase is involved, such as cancer.

This application is based on patent application No. Hei 10-98486 filed in Japan, the content of which is incorporated herein by reference.

BACKGROUND ART

The ends of the chromosomes of eukaryotic cells like those of animal cells are called telomeres, and they have a higher-order structure comprising characteristic repetitive DNA sequences and proteins which are bonded thereto. The telomere structure is considered to have an important role in the stabilization of chromosomes. In cells in which the telomere has become shortened, deletions of chromosome and fusion of the ends of chromosomes with each other are frequently observed. In replication of straight chain DNA, since the RNA primer of the 5' terminal end cannot be replaced by DNA, the chromosome becomes shorter by the primer portion at each replication. Actually, when human somatic cells are cultured and successively passaged, the telomere becomes shortened and the cells finally die due to instability of the chromosomes as mentioned above. In this way, the length of the telomere is known as one factor which regulates the limited division potential which cells have and is known to be closely related to the aging of cells, the immortalization of cells, and the like.

In contrast, the telomeres of protozoa and yeasts which are single cells do not shorten even when they are repeatedly propagated. In these organisms, an RNA dependent DNA polymerase, called telomerase, which lengthens one chain of the telomere repeating sequence, is active, and fixedly maintains the length of the telomere which is shortened along with division. Conventionally, measurement of the telomerase enzyme activity has been difficult because of its low sensitivity but a method (Telomeric Repeat Amplification Protocol; TRAP Method) has been developed which amplifies the reaction products of telomerase by PCR (Kim, N. W., et al., Science, 266, 2011, 1995), and it is possible to measure the telomerase activity of various cells and tissues of higher animals including humans.

Cells derived from human cancer are different from normal cells in that they can proliferate without limit in vitro, and the telomeres do not shorten even with repeated cell division. The results of an investigation of telomerase activity in various human tissues using the above-mentioned TRAP method indicate that telomerase activity, which is not detected in almost all normal human tissues with the exception of reproductive cells and some bone marrow cells, was characteristically detected in cancer tissues (Shay, J. W., et al., Eur. J. Cancer, 33, 787, 1997). These results indicate that the acquisition of a mechanism which avoids shortening of telomeres via telomerase is important in the development of human cancer. Since telomerase is characteristically expressed by cancer cells and concerned with their unlimited proliferation activity, it is expected that a pharmaceutical which blocks the activity will be a highly selective anticancer pharmaceutical.

It is presumed that telomerase is a complex comprising a plurality of units, and the genes for the two structural units, namely, hTR (the human telomerase RNA), which is the RNA molecule which forms the template for extending a strand of the telomere DNA, and hTERT (Human Telomerase Reverse Transcriptase), which is the enzyme subunit which catalyzes the polymerase reaction, have been cloned (Feng, J. et al., Science 269, 1236, 1995; Nakamura, T. M., et al., Science 211, 955, 1997). The relationship between the expression of these units and telomerase activity has been analyzed and it has been reported that the telomerase activity characteristically detected in human cancer tissue is correlated with the expression of the hTERT protein, i.e., the expression of telomerase activity in cancer is regulated by the hTERT protein (Nakamura, T. M., et al., Science 277, 955, 1997; Nakayama, J., et al., Nature Genetics 18, 65, 1998). In addition, it has been shown that, by the introduction of the hTERT gene into normal human cells having dividing life, the life of those cells was extended and it has become clear that hTERT functions as a molecule which regulates cell aging and the immortalization of cells (Bodnar, A. G., et al., Science 279, 349, 1998). In this way, it is expected that analysis of the function of the hTERT protein will provide important information in development of pharmaceuticals not only for cancer but also for disease associated with aging.

As a means for investigating the expression and function of specific proteins in cells and tissues, antibodies having high affinity and specificity to antigen are extremely important in the functional analysis of proteins. As antibodies to the hTERT protein, polyclonal antibodies produced using rabbits are known, and it has been reported that it is possible to detect telomerase activity in a sample obtained by immune precipitation of an extract of human cancer cells (HeLa S3) (Harrington, L., et al., Genes & Dev. 11. 3109, 1997). However, because the amount of hTERT protein expressed is extremely small, it is not possible to detect the hTERT protein expressed within the human cancer cells (HeLe S3) with the Western blotting method using the reported polyclonal antibodies.

DISCLOSURE OF THE INVENTION

The present invention provides a monoclonal antibody which can specifically and efficiently recognize hTERT protein which is the catalytic subunit of telomerase, and provides a human chimeric antibody, a CDR grafted antibody, a single chain antibody, and a disulfide stabilized antibody which contain the monoclonal antibody, and thereby providing detecting and assaying methods for the hTERT protein.

The present invention also provides diagnosis methods, diagnosis agents, and therapeutic agents which use this monoclonal antibody for diseases in which telomerase is involved such as cancer.

The present invention relates to the following items (1) to (37).

(1) A monoclonal antibody which recognizes a human telomerase catalytic subunit.

An object of the present invention is providing superior monoclonal antibodies having high reactivity for the purpose of detecting hTERT protein within cells.

It is sufficient for the monoclonal antibody of the present invention to be one which recognizes human telomerase reverse transcriptase (hereinafter referred to as hTERT), which is the catalytic subunit of telomerase.

Examples of the monoclonal antibodies include antibodies produced by hybridoma, and genetic recombinant antibodies produced by transformants which are transformed by an expression vector containing the antibody gene.

In more detail, it is possible to obtain an anti-hTERT monoclonal antibody by preparing hTERT protein, which is the catalytic subunit of telomerase, or a peptide or the like chemically synthesized based on the amino acid sequence of the hTERT protein [Science, 277, 955(1997)] as an antigen; inducing antibody-producing cells having antigenic specificity from animals immunized with the antigen; fusing them with bone marrow tumor cells to produce hydbridomas; culturing the hybridoma or inducing ascitic cancer in an animal by administering the hybridoma to the animal separating the anti-hTERT monoclonal antibody from culture medium or the ascites and then purifying.

(2) A monoclonal antibody according to the above-mentioned item (1), wherein said monoclonal antibody is obtainable by immunizing an animal with a partial peptide of the human telomerase catalytic subunit, the partial peptide having an amino acid sequence designated as one of SEQ ID NOs: 1, 2, 3, and 6.

(3) A monoclonal antibody according to the above-mentioned item (1), wherein said monoclonal antibody reacts specifically with the amino acid sequence of the human telomerase catalytic subunit, the sequence being designated as one of SEQ ID NOs: 1, 2, 3, and 6.

(4) A monoclonal antibody according to one of the above-mentioned items (1) to (3), wherein said monoclonal antibody is selected from the group consisting of monoclonal antibodies KM 2311, KM2582, KM2590, KM2591, and KM2604.

(5) A hybridoma which produces the monoclonal antibody according to one of the above-mentioned items (1) to (3).

(6) A hybridoma according to the above-mentioned item (5), wherein said hybridoma is selected from the group consisting of KM 2311 (FERM BP-6306), KM2582 (FERM BP-6663), KM2590 (FERM BP-6683), KM2591(FERM BP-6684), and KM2604 (FERM BP-6664).

(7) A monoclonal antibody according to one of the above-mentioned items (1) to (3), wherein said monoclonal antibody is a genetic recombinant antibody.

(8) A monoclonal antibody according to one of the above-mentioned items (7), wherein said genetic recombinant antibody is selected from the group consisting of a humanized antibody and an antibody fragment.

The genetic recombinant antibody of the present invention is the antibody in which the above-mentioned monoclonal antibody of the present invention is modified by means of genetic recombinant techniques. Examples of the genetic recombinant antibodies include antibodies produced by genetic recombination, such as humanized antibodies and antibody fragments. Among the genetic recombinant antibodies, those having the properties of monoclonal antibodies, low antigenicities, and extended half life in blood, are preferable for therapeutic agents.

The humanized antibodies of the present invention include human chimeric antibodies and human CDR (complementary determining region, hereinafter referred to as CDR) grafted antibodies.

The antibody fragments of the present invention include Fab (abbreviation of Fragment of antigen binding), Fab', F(ab')$_2$, a single chain antibody (single chain Fv; hereinafter referred to as scFv), and a disulfide stabilized antibody (disulfide stabilized Fv; hereinafter referred to as dsFv), which are antibody fragments reacting specifically with human hTERT.

(9) A monoclonal antibody according to the above-mentioned item (8), wherein said humanized antibody is a human chimeric antibody.

A human chimeric antibody means an antibody comprising a variable region heavy chain (hereinafter referred to as VH) and a variable region light chain (hereinafter referred to as VL) of an antibody of nonhuman animals, and a constant region heavy chain (hereinafter referred to as CH) and a constant region light chain (hereinafter referred to as CL) of a human antibody.

The human chimeric antibody of the present invention can be produced by obtaining cDNAs coding for VH and VL from hybridomas which produce a monoclonal antibody specifically reacting with human hTERT; constructing an expression vector of human chimeric antibody by inserting the above cDNA to an expression vector for animal cells which contains a gene coding for human antibody CH and human antibody CL, and introducing the vector into animal cells, thereby allowing an expression of the human chimeric antibody of the present invention.

The structure of the C region of the human chimeric antibody of the present invention may belong to any class of immunoglobulin (Ig), preferably being the C region of IgG type, more preferably being C region of IgG1, IgG2, IgG3, IgG4, and the like, which belong to IgG type.

(10) A human chimeric antibody comprising an antibody heavy chain (H chain) variable region (V region) and an antibody light chain (L chain) V region of the monoclonal antibody according to the above-mentioned item (1), and H chain constant region (C region) and L chain C region of a human antibody.

(11) A human chimeric antibody according to the above-mentioned item (10), wherein amino acid sequences of said H chain V region and L chain V region have the same amino acid sequences as the amino acid sequence of an H chain V region and L chain V region of a monoclonal antibody selected from the group consisting of monoclonal antibodies KM 2311, KM2582, KM2590, KM2591, and KM2604.

(12) A monoclonal antibody according to the above-mentioned item (8), wherein said humanized antibody is CDR (complementary determining region) grafted antibody.

The human CDR grafted antibody means an antibody in which CDR of VH and VL of human antibody are substituted with the CDR sequence of an antibody of nonhuman animals, respectively.

The human CDR grafted antibody of the present invention can be produced by constructing cDNA coding for the V region in which CDR sequences of VH and VL of any human antibody are substituted respectively with the CDR sequence of an antibody, specifically reacting with human hTERT, of nonhuman animals; constructing an expression vector of human CDR grafted antibody by inserting the cDNAs to an expression vector for animal cells which contains a gene coding for human antibody CH and human antibody CL, respectively; and introducing the vector into animal cells, thereby allowing an expression of the antibody.

The structure of the C region of the human CDR grafted antibody of the present invention may belong to the C region of any class of immunoglobulin (Ig), but preferably to the C region of IgG type, more preferably to the C region of IgG1, IgG2, IgG3, IgG4, and the like, which belong to the IgG type.

(13) A CDR grafted antibody comprising V region complementary determining regions of H chain and L chain of the monoclonal antibody according to the above-mentioned item (1), and C region and V region framework regions of an H chain and L chain of a human antibody.

(14) A CDR grafted antibody according to the above-mentioned item (13), wherein the amino acid sequences of said complementary determining regions of the H chain V region and L chain V region have the same amino acid sequence as the amino acid sequences of complementary determining regions of an H chain V region and L chain V region of a monoclonal antibody which is selected from the group consisting of monoclonal antibodies KM 2311, KM2582, KM2590, KM2591, and KM2604.

(15) A monoclonal antibody according to the above-mentioned item (8), wherein said antibody fragment is an antibody selected from the group consisting of Fab, Fab', F(ab')$_2$, a single chain antibody, and disulfide stabilized Fv.

Fab has a molecular weight of approximately fifty thousand and an antigen binding activity, consisting of whole L chain and a portion corresponding approximately to half of an H chain on an N terminal region thereof, is obtained by enzymatic degradation of papain at a peptide portion above two disulfide bonds bridging two H chains at the hinge region of IgG.

Fab of the present invention can be obtained by treating an antibody which specifically reacts with human hTERT with papain. Alternatively, Fab can be obtained by inserting DNA coding for a Fab fragment of the antibody into an expression vector for animal cells; and introducing the vector into animal cells, thereby allowing an expression of the fragment.

Fab' has a molecular weight of approximately fifty thousands and an antigen binding activity, and is a fragment after cleaving disulfide bonds between the hinge of the above-mentioned F(ab')$_2$.

Fab' of the present invention can be obtained by treating an antibody which specifically reacts with human hTERT with reducing agent, dithiothreitol. Alternatively, Fab' of the present invention can be obtained by inserting DNA coding for a Fab' fragment of the antibody to an expression vector for animal cells; and introducing the vector into animal cells, thereby allowing an expression of the fragment.

F(ab')$_2$ has a molecular weight of approximately one hundred thousand and an antigen binding activity, consisting of two Fab regions combined each other at the hinge region, which are obtained by enzymatic degradation of trypsin at a portion below two disulfide bonds at the hinge region of IgG.

F(ab')$_2$ of the present invention can be obtained by treating an antibody which specifically reacts with human hTERT with trypsin. Alternatively, F(ab')$_2$ can be obtained by inserting DNA coding for a F(ab')$_2$ fragment of the antibody into an expression vector for animal cells; and introducing the vector into animal cells, thereby allowing an expression of the fragment.

(16) A single chain antibody comprising an H chain V region and L chain V region of the monoclonal antibody according to the above-mentioned item (1).

A single chain antibody (scFv) means a VH-L-VL or VL-L-VH polypeptide wherein a single VH and a single VL are linked using an appropriate peptide linker (hereinafter referred to as L), a VH-L-VL or VL-L-VH polypeptide. As VH and VL contained in the scFv of the present invention, any of a monoclonal antibody or a human CDR grafted antibody of the present invention can be used.

The scFv of the present invention can be produced by obtaining cDNAs coding for VH and VL from hybridomas or transformants which produce an antibody specifically reacting with human hTERT; constructing an expression vector for a single chain antibody and then inserting the above cDNAs into the vector; and introducing the expression vector into *Escherichia coli*, yeast, or animal cells to allow expression of the antibody.

(17) A single chain antibody according to the above-mentioned item (16), wherein the amino acid sequences of an H chain V region and L chain V region of said single chain antibody have the same amino acid sequence as the amino acid sequences of an H chain V region and L chain V region of a monoclonal antibody which recognizes the human telomerase catalytic subunit.

(18) A single chain antibody according to the above-mentioned item (17), wherein the amino acid sequences of an H chain V region and L chain V region of said single chain antibody have same amino acid sequence as the amino acid sequences of an H chain V region and L chain V region of a monoclonal antibody which is selected from the group consisting of monoclonal antibodies KM 2311, KM2582, KM2590, KM2591, and KM2604.

(19) A single chain antibody according to the above-mentioned item (16), wherein the amino acid sequences of an H chain V region and L chain V region of said single chain antibody have same amino acid sequences as the amino acid sequences of said complementary determining regions of an H chain V region and L chain V region of a monoclonal antibody which recognizes the human telomerase catalytic subunit.

(20) A single chain antibody according to the above-mentioned item (19), wherein the amino acid sequences of an H chain V region and L chain V region of said single chain antibody have same amino acid sequence as the amino acid sequences of said complementary determining regions of an H chain V region and L chain V region of a monoclonal antibody which is selected from the group consisting of monoclonal antibodies KM 2311, KM2582, KM2590, KM2591, and KM2604.

(21) A disulfide stabilized antibody comprising an H chain V region and L chain V region of monoclonal antibody according to the above-mentioned item (1).

The disulfide stabilized antibody (dsFv) means an antibody in which polypeptides in which one amino acid in VH and one amino acid in VL each are substituted with a cysteine residue, are combined via a disulfide bond. The amino acid to be substituted with a cysteine residue can be selected based on prediction of the stereochemical structure of the antibody according to a method described by Reiter (Protein Engineering, 7, 697 (1994)). For the VH or VL contained in the disulfide stabilized antibody, both of a monoclonal antibody and human CDR grafted antibody can be used.

The disulfide stabilized antibody of the present invention can be produced by obtaining cDNAs coding for VH and VL from hybridomas or transformants which produce an antibody specifically reacting with human hTERT; inserting the above cDNAs into an appropriate expression vector; and introducing the expression vector into *Escherichia coli*, yeast, or animal cells to allow an expression of the antibody.

(22) A disulfide stabilized antibody according to the above-mentioned item (21), wherein the amino acid sequences of an H chain V region and L chain V region of said disulfide stabilized antibody have the same amino acid sequence as the amino acid sequences of an H chain V region and L chain V region of a monoclonal antibody which recognizes the human telomerase catalytic subunit.

(23) A disulfide stabilized antibody according to the above-mentioned item (22), wherein the amino acid sequences of an H chain V region and L chain V region of said disulfide stabilized antibody have the same amino acid sequence as the amino acid sequences of an H chain V region and L chain V region of a monoclonal antibody which is selected from the group consisting of monoclonal antibodies KM 2311, KM2582, KM2590, KM2591, and KM2604.

(24) A disulfide stabilized antibody according to the above-mentioned item (21), wherein the amino acid sequences of an H chain V region and L chain V region of said disulfide stabilized antibody have the same amino acid sequence as the amino acid sequences of said complementary determining regions of H chain V region and L chain V region of a monoclonal antibody which recognizes the human telomerase catalytic subunit.

(25) A disulfide stabilized antibody according to the above-mentioned item (24), wherein the amino acid sequences of an H chain V region and L chain V region of said disulfide stabilized antibody have the same amino acid sequence as the amino acid sequences of said complementary determining regions of an H chain V region and L chain V region of a monoclonal antibody which is selected from the group consisting of monoclonal antibodies KM 2311, KM2582, KM2590, KM2591, and KM2604.

(26) An antibody characterized in that said antibody according to one of the above-mentioned items (1) to (3), (10), (11), (13), (14), and (16) to (25) is bound to a radioactive isotope, a protein, or a low molecular agent by chemical or genetic engineering means.

The fusion antibody means an antibody in which the above-mentioned antibody is bound to a radioactive isotope, a protein, or a low molecular agent by chemical or genetic engineering means.

The fusion antibody of the present invention can be produced by chemically combining an antibody which reacts specifically with human hTERT with a radioactive isotope, a protein, a low molecular agent, or the like. Alternatively, the protein-fusion antibody can be produced by ligating cDNA coding for the protein to cDNA coding for the antibody; inserting the above cDNAs into an appropriate expression vector; and introducing the expression vector into *Escherichia coli*, yeasts, or animal cells to allow an expression of the antibody.

(27) A method for immunologically detecting a human telomerase catalytic subunit using the monoclonal antibody according to one of the above-mentioned items (1) to (3), (10), (11), (13), (14), and (16) to (26).

(28) An immunological detecting method according to the above-mentioned item (27), wherein the method is Western blotting, immunohisto staining method, immunocyte staining method, or dot blotting.

(29) A method for immunologically detecting a microorganism, an animal cell, or an insect cell which expresses a human telomerase catalytic subunit intracellularly or extracellularly, using the monoclonal antibody according to one of the above-mentioned items (1) to (3), (10), (11), (13), (14), and (16) to (26).

(30) An immunological detecting method according to the above-mentioned item (29), wherein the method is Western blotting, immunohisto staining method, immunocyte staining method, or dot blotting.

(31) A method for immunologically quantitating a human telomerase catalytic subunit using the monoclonal antibody according to one of the above-mentioned items (1) to (3), (10), (11), (13), (14), and (16) to (26).

(32) An immunological quantitating method according to the above-mentioned item (31), wherein the method is fluorescent antibody method, enzyme-linked immunosorbent assay method (ELISA), radioimmunoassay (RIA), or sandwich ELISA method.

(33) A method for immunologically quantitating a microorganism, an animal cell, or an insect cell which expresses human telomerase catalytic subunit intracellularly or extracellularly, using the monoclonal antibody according to one of the above-mentioned items (1) to (3), (10), (11), (13), (14), and (16) to (26).

(34) An immunological quantitating method according to the above-mentioned item (33), wherein the method is fluorescent antibody method, enzyme-linked immunosorbent assay method (ELISA), radioimmunoassay (RIA), or sandwich ELISA method.

(35) A diagnosis method for diseases wherein telomerase is involved using the monoclonal antibody according to one of the above-mentioned items (1) to (3), (10), (11), (13), (14), and (16) to (26).

(36) A diagnosis agent for diseases wherein telomerase is involved using the monoclonal antibody according to one of the above-mentioned items (1) to (3), (10), (11), (13), (14), and (16) to (26).

(37) A therapeutic agent for diseases wherein telomerase is involved using the monoclonal antibody according to one of the above-mentioned items (1) to (3), (10), (11), (13), (14), and (16) to (26).

In the following, the present invention will be explained in more detail.

1. The Manufacturing Method for Anti-human Telomerase Catalytic Subunit (hTERT) Monoclonal Antibodies (1) Preparation of Antigen Examples of antigens include a cell which intracellularly expresses hTERT, which is the anti-human telomerase catalytic subunit, or a fraction thereof; an hTERT protein which is a telomerase catalytic subunit with different length of amino acids, fusion protein thereof to Fc portion of an antibody can be mentioned.

As a cell which intracellularly expresses hTERT, anti-human telomerase catalytic subunit, Namalwa cell (J. Biol. Chem., 269, 14730(1994)), CHO cell (ATCC No.CCL-61), and the like can be mentioned.

The above-mentioned cell itself can be used as an antigen; and a fraction of the telomerase catalytic subunit hTERT, which is fractionated from the cell by using usual separation and purification methods for enzymes, as described below, can be also used as an antigen.

Furthermore, the telomerase catalytic subunit hTERT protein, a telomerase catalytic subunit hTERT protein with different amino-acid-length, or fusion protein thereof fused to Fc portion of an antibody, which are expressed with the DNA coding for the telomerase catalytic subunit hTERT obtained from the above-mentioned cell using genetic engineering means, can be used as an antigen. The explanation of the detailed method follows.

For obtaining the DNA coding for the telomerase catalytic subunit hTERT, a cDNA library is prepared by using a general method [Molecular Cloning $2^{nd}$ edition, Cold Spring Harbor Laboratory, Press New York (1989) (hereinafter referred to as Molecular Cloning $2^{nd}$ edition) or Current Protocols in Molecular Biology Supplement 1–38 (hereinafter referred to as Current Protocols)] from the cDNA described in the literature [Science, 277, 955(1997)] or from the above-mentioned cells expressing the telomerase catalytic subunit hTERT intracellularly.

In more detail, the cDNA library is prepared by extracting RNA, synthesizing cDNA from the RNA, and incorporating the cDNA into a cloning vector, and introducing it into a host cell.

DNA coding for hTERT can be obtained by selecting a transformant containing the desired cDNA from the library.

As a method for preparing the total RNA from the cell expressing telomerase catalytic subunit hTERT intracellularly, guanidine/caesium chloride method, guanidine thiocyanate method [Methods in Enzymol., 154, 3(1987)], and the like can be mentioned. As a method for preparing mRNA from the total RNA, the column method or batch method using oligo dT cellulose, or the like can be used. In addition, mRNA can be prepared using a kit such as the First Truck mRNA Isolation Kit (manufactured by Invitrogen Co.), or the Quick Prep mRNA Purification Kit (manufactured by Pharmacia Co.).

As a method for sythesizing cDNA from the obtained RNA, the Okayama-Berg method [Mol. Cell. Biol., 2, 161(1982)] and Gublar-Hoffmann method [Gene, 25, 263 (1983)], or the like can be mentioned. The cDNA can be also synthesized using a kit, such as the Superscript Plasmid System for cDNA Synthesis and Plasmid Cloning (manufactured by Gibco BRL Co.), or the ZAP-cDNA Synthesis Kit (manufactured by Stratagene Co.).

As a cloning vector for incorporating cDNA thereto, any vectors which can be replicated and stably maintain cDNA in a host gene are available, examples thereof including a phage vector, a plasmid vector, or the like. Particulary, ZAP Express [manufactured by Stratagene Co.; Strategies, 5, 58(1992)], pBluescript II SK(+) [Nucleic Acids Research, 17, 9494(1989)], λ zap II (manufactured by Stratagene Inc.), λ gt10, λ gt11 [DNA Cloning, A Practical Approach, 1, 49(1985)], λ TriplEx (manufactured by Clonetech Inc.), λ EXCell (manufactured by Pharmacia Inc.), pT7T3 18U (manufactured by Pharmacia Inc.), pcD2 [Mol. Cell. Biol., 3, 280(1983)], pUC18 [Gene, 33, 103(1985)], pAMo [J. Biol. Chem., 268, 22782(1993); alias pAMoPRC3Sc (Japanese Unexamined Patent Application, First Publication No. Hei 5-336963)], or the like can be used.

As a host microorganism, any microorganism which belongs to the genus of *Escherichia coli* can be used. Particulary, *Escherichia coli* XLI-Blue MRF' [manufactured by Stratagene Inc.; Strategies, 5, 58(1992)], *Escherichia coli* C600 [Genetics, 39, 440(1954)], *Escherichia coli* Y1088 [Science, 222, 778(1983)], *Escherichia coli* Y1090 [Science, 222, 778(1983)], *Escherichia coli* NM522 [J. Mol. Biol., 166, 1(1983)], *Escherichia coli* K802 [J. Mol. Biol., 16, 118(1966)], *Escherichia coli* JM105 [Gene, 3, 275 (1985)], *Escherichia coli* SOLR™ Strain [commercially available from Stratagene Inc.], *Escherichia coli* LE392 (Molecular Cloning 2$^{nd}$ Edition), or the like can be used.

The cDNA library is prepared by incorporating cDNA into the above-mentioned cloning vector, and introducing the cloning vector into a host cell.

When a plasmid is used as a cloning vector, it is introduced into a host cell by electropolation method, calcium chloride method, or the like. When a phage is used as a cloning vector, it is introduced into a host cell by an in vitro packaging method or the like.

From the obtained cDNA library, a transformant which contains the DNA coding for the telomerase catalytic subunit hTERT can be obtained by preparing a probe based on a base sequence of DNA coding for the telomerase catalytic subunit hTERT, as described in the literature [Science, 277, 955(1997)], for example; labeling the probe with fluorescent material, radiation, enzymes or the like; and conducting a plaque hybridization, a colony hybridazation, Southern hybridazation, or the like to select a hybridizing transformant.

The obtained cDNA with full length or a partial fragment thereof which codes for the telomerase catalytic subunit hTERT [Science, 277, 955(1997)] is inserted at site downstream of the promoter in an appropriate vector to construct a recombinant vector. Then, the recombinant vector is introduced into a host cell and thereby the cell expressing the telomerase catalytic subunit hTERT is obtained. By culturing the cell expressing the telomerase catalytic subunit hTERT in an appropriate medium, the telomerase catalytic subunit hTERT with full length or a partial fragment thereof can be produced as an intact protein or a fusion protein within the cell or in the culture supernatant.

As a host, any cells which can express the desired gene can be used, examples thereof including bacteria, yeast, animal cells, insect cells, or the like. As bacteria, bacteria such as Escherichia genus and Bacilli like *Escherichia coli, Bacillus subtilis*, and the like can be mentioned. As yeast, *Saccharomyces cerevisiae, Schizosaccharomyces pombe* or the like can be mentioned. As animal cells, human cells such as Namalwa cells, monkey cells such as COS cell, chinese hamster cells such as CHO cells can be mentioned. As insect cells, Sf9, Sf21 (manufactured by Pharmingen Co.), and High Five (manufactured by Invitrogen Co.) can be mentioned.

As a vector for introducing the DNA of the present invention, any vector which can incorporate the DNA therein and be expressed in a host cell can be employed.

When bacteria, such as *Escherichia coli*, is used as a host cell, an expression vector which comprises a promoter, a ribosome binding sequence, the DNA of the present invention, a transcription terminal sequence, and if necessary a regulation sequence of the promoter is suitable. Examples thereof include commercially available pGEX (manufactured by Pharmacia Inc.) and pET system (manufactured by Novagen Inc.) or the like.

For introducing the recombinant vector into bacteria, any method for introducing DNA into bacteria can be used, examples thereof including a method using calcium ions [Proc. Natl. Acad. Sci., USA, 69, 2110(1972)], the protoplast method (Japanese Unexamined Patent Application, First Publication No. Sho 63-248394), or the like.

When using yeast as a host, YEp13(ATCC37115), YEp24 (ATCC37051), YCp50 (ATCC37419) and the like are available as an expression vector, for example.

For introducing the recombinant vector into yeast, any method for introducing DNA into yeast can be used, examples thereof including the electropolation method [Methods. Enzymol., 194, 182(1990)], spheroplast method [Proc. Natl. Acad. Sci., USA, 84, 1929(1978)], lithium acetate method [J. Bacterial., 153, 163(1983)], or the like.

When using an animal cell as a host, pAGE107 [Japanese Unexamined Patent Application, First Publication No. Hei 3-22979; Cytotechnology, 33, 133(1990)], pAGE103[J. Biochem. 101, 1307(1987)] or the like is available as an expression vector, for example.

As a promoter, any promoters which can be expressed in an animal cell can be used, examples thereof including IE (immediate early) gene promoter of cytomegalovirus (CMV), SV40, promoter of metallothionein or the like, for example. The enhancer of the IE gene of human CMV may be used in addition to a promoter.

For introducing a recombinant vector into animal cells, any method for introducing DNA into animal cells can be used, examples thereof including the electropolation method [Cytotechnology, 3, 133(1990)], calcium phosphate method (Japanese Unexamined Patent Application, First Publication No. Hei 2-227075), lipofection method [Proc. Natl. Acad. Sci., USA, 84, 7413(1987)] or the like, for example.

When using an insect cell as a host, the protein can be expressed by a method described in Current Protocols (Supplement 1–34), Baculovirus Expression Vectors, A laboratory Manual) or the like. In more detail, a recombinant gene-introducing vector, as mentioned below, and baculovirus are co-introduced into an insect cell, and thereby a recombinant virus is obtained in a culture supernatant of the insect cells. Then, insect cells are infected with the recombinant virus and thereby the insect cell expressing the protein is obtained.

As a vector for introducing the gene, pVL1392, pVL1393, pBlueBacIII (all are manufacutured by Invitrogen Inc.) or the like are available, for example.

As baculovirus, Autograoha californica nuclear polyhedrosis, which is capable of infecting an insect belonging to Noctuidae or the like is available, for example.

As a method for co-introducing the above-mentioned recombinant gene-introducing vector and baculovirus for preparing a recombinant virus, the calcium phosphate method (Japanese Unexamined Patent Application, First Publication No. Hei 2-227075), lipofection method [Proc. Natl. Acad. Sci., USA, 84, 7413(1987)] or the like can be used, for example.

Furthermore, the protein can be produced by constructing recombinant baculovirus using the Baculo Gold Starter Kit (manufactured by Pharmingen Inc.) or the like, and infecting insect cells such as the above-mentioned Sf9, Sf21, High Five or the like with the recombinant virus [Bio/Technology, 6, 47(1988)].

As a method for expressing the gene, methods, such as secretion production, expression of fusion protein or the like, have been developed, and any of them can be used as well as direct expression. These methods can be conducted based on the method described in Molecular Cloning $2^{nd}$ Edition, for example.

As a protein to be fused, β-galactosidase, protein A, IgG binding region of protein A, chloramphenicol acetyltransferase, poly(Arg), poly(Glu), protein G, maltose binding protein, glutathione S-transferase, polyhistidine chain (His-tag), S peptide, DNA binding protein domain, Tac antigen, thioredoxin, green fluorescent protein, any antibody epitope, or the like can be mentioned [Akio Yamakawa, Experimental Medical Science, 13, 469–474 (1995)].

By culturing the obtained transformant as described above in a medium, thereby allowing the production and accumulation of the telomerase catalytic subunit hTERT with full length or a partial fragment thereof as an intact protein or a fusion protein, and collecting it from the culture, the telomerase catalytic subunit hTERT with full length or a partial fragment thereof can be produced as an intact protein or a fusion protein.

The method for culturing the transformant of the present invention in a medium is conducted according to a general method for culturing a host.

As a medium for culturing the transformant obtained in microorganism such as *Escherichia coli* or yeast, as a host, any medium is available in which a carbon source, a nitrogen source, inorganic salts, or the like, which are capable of being assimilated by the microoranism, are contained and in which the transformants can be effectively cultured, examples thereof including natural medium and synthetic medium (Molecular Cloning, $2^{nd}$ Edition). The culturing is carried out in aerobic condition, such as a normal shake culture, a depth aeration agitation culture or the like, for 16~96 hours at 15~40° C. During the culturing, the pH of the medium is maintained between 3.0 and 9.0. The pH is adjusted using an inorganic or organic acid, alkaline solution, urea, calcium carbonate, ammonia, or the like. During the culturing, antibiotics such as ampicillin or tetracycline may be added into the medium, if necessary.

As the medium for culturing the transformants obtained in animal cells as a host, a general medium can be used, examples thereof including RPMI1640 medium, Eagle's MEM medium, these medium to which fetal calf serum or the like is added, for example. The culturing is generally carried out in the presence of 5% $CO_2$, for 3 to 7 days at 35 to 37° C. During the culturing, antibiotics such as kanamycin or penicillin may be added into the medium, if necessary.

As the medium for culturing the transformants obtained in an insect cell as a host, a general medium can be used, examples thereof including TNM-FH medium (manufactured by Pharmingen Co.), Sf900IISFM (Life Technologies Co.), ExCell400, ExCell405 (both are manufactured by JRH Biosciences Co.), or the like. The culturing is carried out for 1 to 4 days at 25 to 30° C. During the culturing, antibiotics such as gentamycin may be added into the medium, if necessary.

In the above, when it is possible to culture in serum-free medium for animal cells and insect cells, the serum-free medium is preferred because the purification of the telomerase catalytic subunit hTERT with full length or a partial fragment thereof as an intact protein or a fusion protein becomes easier.

When the telomerase catalytic subunit hTERT with full length or a partial fragment thereof is accumulated within the host cells as an intact protein or a fusion protein, after culturing, the cells are centrifuged, suspended in an aqueous buffer, disrupted by the ultrasonic method, French press method or the like, and centrifuged to collect the protein in the supernatant.

Furthermore, when an insoluble body is formed in the cell, the insoluble body is solubilized with a protein denaturant, diluted or dialyzed in a solution with no protein denaturant or with a lowered content thereof so that denaturation of the protein does not occur, thereby making it possible to form the stereochemical structure of the protein.

When the telomerase catalytic subunit hTERT with full length or a partial fragment thereof is secreted outside of the cell as an intact protein or a fusion protein, the expressed protein can be collected in the culture supernatant. For the isolation and purification, separating operations such as solvent extraction, fractional precipitation by organic solvents, salting out, dialysis, centrifugation, ultrafiltration, ion-exchange chromatography, gel filtration chromatography, hydrophobic chromatography, affinity chromatography, reversed phase chromatography, crystallization, electrophoresis, or the like, in alone or a combination thereof, can be conducted.

Alternatively, as the polypeptide having a partial sequence, a protein partial sequence of 5 to 30 residues is selected. In order to obtain an antibody which can recognize a protein having a natural structure, it is necessary to select a partial sequence which is present on the surface of the protein from the point of view of the quaternary structure. As a method for predicting partial sequences which are present on the surface of a protein form the point of view of the quaternary structure, commercially available protein sequence analysis software, such as Genetyx Mac, and the like can be mentioned. In general, hydrophobic part of the amino acid residues is in the internal region of the structure of a protein, and hydrophilic part of the amino acid residues is on the protein surface. In addition, situations the N-terminal region and the C-terminal region of the protein are present on the protein surface. However, partial peptides selected in this way do not always give rise to antigens which produce the desired antibodies.

In partial peptides, cysteine is added to the ends for the purpose of cross-linking with the carrier protein which will be discussed below. When an internal sequence of the protein is selected, as necessary, the N-terminal peptides are acetylized and the C-terminal peptides are amidated.

Partial peptides can be synthesized by means of general liquid phase peptide synthesis methods, solid phase peptide synthesis methods, methods which are appropriate combinations of these methods, or methods which are based on them [refer to The Peptides, Analysis, Synthesis, Biology, Vol. 1, edited by Erhard Gross and Johannes Meinhofer, Academic Press, 1979, Vol. 2, 1980, Vol. 3, 1981; Foundations and Experiments in Peptide Synthesis, Nobuo Izumiya et al., Maruzen, 1985; Development of Pharmaceuticals, New Series, Volume 14, Peptide Synthesis, compiled by Haruaki Yajima, Hirokawa Shoten, 1991; and International Journal of Peptide Protein Research, Vol. 35, page 161 (1990)].

In addition, it is also possible to synthesize partial peptides using an automatic peptide synthesizer. The synthesis of peptides with a peptide synthesizer can be carried out with commercially available peptide synthesizers such as the peptide synthesizer manufactured by Shimadzu Seisakusho, peptide synthesizers manufactured by Applied Biosystems, Inc., USA, (hereinafter referred to as ABI Inc.), and peptide synthesizers manufactured by Advanced ChemTech Inc., USA (hereinafter referred to as ACT Inc.), using Nα-Fmoc-amino acid or N α-Boc-amino acid in which side chains are suitably protected, or the like and respective programs for synthesis.

The protective amino acids and carrier resins used as the starting materials can be obtained from ABI Inc., Shimadzu Seisakusho, Kokusan Chemicals (KK), Nova Biochem, Watanabe Chemicals (KK), ACT Inc., Peptide Kenkyusho (KK) or the like. In addition, the protective amino acids, protective organic acids and protective organic amines which form Compounds 1 to 3 mentioned below can be synthesized according to reported synthesis methods or based on them [refer to The Peptides, Analysis, Synthesis, Biology, Vol. 1, edited by Erhard Gross and Johannes Meinhofer, Academic Press, 1979, Vol. 2, 1980, Vol. 3, 1981; Foundations and Experiments in Peptide Synthesis, Nobuo Izumiya et al., Maruzen, 1985; Development of Pharmaceuticals, New Series, Volume 14, Peptide Synthesis, compiled by Haruaki Yajima, Hirokawa Shoten, 1991; and International Journal of Peptide Protein Research, Vol. 35, page 161 (1990)].

(2) Immunization of Animals and Preparation of Antigen Producing Cells

The obtained protein in the above is used as an antigen for the immunization. For the method of immunization, an intact antigen may be administrated subcutaneously, intravenously, or intraperitoneally, but preferably an antigen is combined with a carrier protein with high antigenicity or an antigen is administrated together with a suitable adjuvani.

Examples of carrier proteins include hemocyanin of Fissurellidae, keyhole limpet hemocyanin, bovine serum albumin, bovine thyroalbumin, or the like. Examples of adjuvants include Complete Freund's Adjuvant, hydroxylated aluminum gel, pertussis vaccine, or the like.

As the, animals used in the immunization, mammals other than human, such as rabbits, goats, mice, rats, hamsters, or the like can be mentioned.

Administration of the antigen is carried out every 1 to 2 weeks after the first administration for 3 to 10 times. A dosage of the antigen is preferably 50~100 μg per animal. On the third to seventh day after each administration, blood sample is collected from the venous plexus of the fundus oculi (eyegrounds) or caudal vein of the immunized animal, and reactivity of the serum with the antigen is confirmed by means of enzyme-linked immunosorbent assays [Enzyme-linked Immunosorbent Assays (EILISA method): published by Igaku Shoin (1976)].

Then, nonhuman mammals whose serum shows sufficient antibody titer with respect to the antigen used in the immunization are offered as sources of serum or antibody producing cells.

It is possible to prepare a monoclonal antibody by fusing the antibody producing cells with bone marrow tumor cells derived from nonhuman mammals to produce hydbridomas, culturing the hybridoma or inducing ascitic cancer in an animal by administering the hybridoma to the animal, then separating and purifying the ascites or culture medium.

The antibody producing cells are collected form spleen cells, lymphonodus, peripheral bloods, or the like, of nonhuman mammals administrated with the antigen.

(3) Preparation of Myeloma Cells

As the myeloma cells, any myeloma cells which are capable of growing in vitro are available, examples thereof including those established cell lines obtained from mice, such as 8-azaguanine-resistant mice (BALB/c origin) myeloma cell lines P3-X63Ag8-U1 (P3-U1) [Eur. J. Immunol., 6: 511(1976)], SP2/0-Ag14 (Sp-2) [Nature, 27, 269(1978)], P3-X63-Ag 8653 (653) (J. Immunol., 123, 1548(1979)], P3-X63-Ag8(X63) [Nature, 256, 495(1975)] or the like. With regard to the culturing and passaging of these established cell lines, a cell number of $2 \times 10^7$ is ensured until cell fusion time according to the known methods (Antibodies, A Laboratory Manual, Cold Spring Harbor Laboratory, Chapter 8, 1988; hereinafter referred to as Antibodies).

(4) Cell Fusion and Selection of Monoclonal Antibody

After washing the myeloma cells and the antibody producing cells obtained above, a cell agglutinative medium, such as polyethylene glycol—1000 (PEG-1000) is added, the cells are made to fuse, and suspended within the culture medium. In the washing of the cells, MEM medium or PBS (1.83 g of disodium hydrogenphosphate, 0.21 g of potassium dihydrogenphosphate, 7.65 g of sodium chloride, and 1 liter of distilled water, pH 7.2) or the like can be used. In addition, as the medium in which the fused cells are suspended, HAT medium (a medium wherein hypoxanthine ($10^{-4}$M), thymidine ($1.5 \times 10^{-5}$M) and aminopterin ($4 \times 10^{-7}$M) are added to normal medium [a medium wherein glutamine (1.5 mM), 2-mercaptoethanol ($5 \times 10^{-5}$M), gentamicin (10 μg/ml) and fetal calf serum (FCS) (10% manufactured by CSL Co.) are added to RPMI-1640 medium]) can be used in such a way that only the desired fused cells are obtained.

After the culturing, a portion of the culture supernatant is taken, and a sample is selected which reacts with the antigenic protein and which does not react with non-antigenic protein by enzyme-linked immunosorbent assays. Next, cloning is carried out by means of limiting dilution analysis, and those determined to have a stable and high antibody value by enzyme-linked immunosorbent assay are selected as monoclonal antibody-producing hybridoma cell lines.

Enzyme-linked Immunosorbent Assays

Antigenic proteins or cells that express the antigenic protein are coated on a 96-well plate and reacted with, as the first antibody, the refined antibodies obtained by the above-described method or hybridoma culture supernatant. After the reaction of first antibody, the plate is washed, and the second antibody is added.

The second antibody is an antibody which is capable of recognizing the immunoglobulin of the first antibody and is labelled with biotin, enzyme, chemiluminescent substances, radioactive compounds, or the like. For example, when a mouse is used for preparation of hybridomas, an antibody which can recognize mouse immunoglobulin is used as the second antibody.

After the reaction, the reaction in accordance with a material which labels the second antibody is conducted, and hybridomas which produce a monoclonal antibody which reacts specifically with the antigen are selected.

As specific examples of the hybridoma cell lines of the present invent ion, hybridoma cell lines KM2311, KM2582, KM2604, KM2590, and KM2591 can be mentioned. Hybridoma cell line KM2311 was deposited with the National Institute of Bioscience and Human-Technology, Agency of Industrial Science and Technology (1–3, Higashi 1 chome Tsukuba-shi, Ibaraki-ken, JAPAN) as FERM BP-6306 on Mar. 24, 1998; hybridoma cell lines KM2382 and KM2604 were deposited with the National Institute of Bioscience and Human-Technology, Agency of Industrial Science and Technology as FERM BP-6663 and FERM BP-6664, respectively, on Feb. 26, 1999; hybridoma cell lines KM2590 and KM2591 were deposited with the National Institute of Bioscience and Human-Technology, Agency of Industrial Science and Technology as FERM BP-6683 and FERM BP-6684, respectively, on Mar. 19, 1999.

(5) Preparation of Monoclonal Antibodies

Monoclonal antibodies can be prepared from the culture solution obtained by culturing hybridoma cells or by peritoneally administering monoclonal antibody producing hybridoma cells to 8 to 10 week-old mice or nude mice which have been pristane treated (intraperitoneally administering 0.5 ml of 2,6,10,14-tetramethylpentadecane (Pristane) and then rearing for two weeks), and then isolation and purification from the ascites in which cancer has been induced.

For the isolation and purification of monoclonal antibodies, the following methods can be used singly or in combination: centrifugation, salting out with 40–50% saturated ammonium sulfate, caprylic acid precipitation, chromatography using a DEAE-sepharose column, a negative ion exchange column, a protein A (or G)-column, a gel filtration column, or the like. By the above methods, the IgG or IgM fractions are collected and purified monoclonal antibody is obtained.

Determination of the subclass of the purified monoclonal antibody can be carried out using a monoclonal antibody typing kit or the like. The amount of protein can be determined by the Lowry method or by calculation based on the optical density at 280 nm.

The subclass of antibodies means isotypes in the classes; IgG1, IgG2a, IhG2b, and IgG3 in mouse, and IgG1, IgG2, IgG3, and IgG4 in human can be mentioned.

Mouse IgG1 and IgG2a types and human IgG1 type have complement-dependent cytotoxicity (hereinafter referred to as CDC activity) and antibody-dependent cellular cytotoxicity (hereinafter referred to as ADCC activity) so that they can be advantageously applied to medical treatments.

2. Method for Preparing Recombinant Antibodies
(I)—Method for Preparing Anti-human hTERT Humanized Antibodies (1) Construction of Expression Vector for Humanized Antibody An expression vector for humanized antibodies, which is necessary for the preparation of humanized antibodies from a nonhuman animal antibody, is constructed. An expression vector for humanized antibodies is an expression vector for animal cells, wherein genes coding for CH and CL, which are the C region of a human antibody, are incorporated. An expression vector for humanized antibodies is constructed by inserting the genes coding for CH and CL of a human antibody, into the expression vector for animal cells, respectively.

As the C region of a human antibody, any C region of a human antibody can be used, examples thereof including Cγ1 and Cγ4 in a human antibody H chain, C κ in a human antibody L chain, or the like. As a gene coding for the C region of human antibodies, chromosomal DNA consisting of exon and intron, or cDNA can be used. As the expression vectors for animal cells, any vectors are available which can incorporate a gene coding for the C region of a human antibody and can be expressed can be used.

For example, pAGE107 [Cytotechnology, 3, 133 (1990)], pAGE103 [J. Biochem., 101, 1307 (1987)], pHSG274 [Gene, 27, 223 (1984)], pKCR [Proc. Natl. Acad. Sci., 78, 1527 (1981)], pSG1 β d2-4 [Cytotechnology, 4, 173 (1990)], or the like can be mentioned. Examples of promoters and enhancers used in an expression vector for animal cells include an initial promoter and enhancer of SV40 [J. Biochem., 101, 1307 (1987)], LTR prompter and enhancer of Moloney's mouse leukemia virus [Biochem. Biophys. Res. Comun., 149, 960 (1987)], the promoter [Cell, 41, 479 (1985)] and enhancer [Cell, 33, 717 (1983)] of immunoglobulin H chain, or the like.

As an expression vector for humanized antibodies, either type of vectors are available: vectors with antibody H chain and L chain on separate vectors, or vectors with antibody H chain and L chain on the same vector (tandem type). However, from the view point of ease of construction of the expression vector for humanized antibodies, ease of the introduction into animal cells, and the balance of the expression amount of antibody H chain and L chain in animal cells, the tandem type expression vectors for humanized antibodies are preferred [J. Immunol. Methods, 167, 271 (1994)].

(2) Obtaining cDNA Coding for VH and VL of a Nonhuman Animal Antibody cDNA coding for VH and VL of a nonhuman animal antibody, a mouse for example, can be obtained as follows.

mRNA is extracted from cells which produce anti-human hTERT monoclonal antibodies, for example, mouse hybridomas which produce anti-human hTERT antibodies, and the extract mRNA is used to synthesize cDNA. The synthesized cDNA is inssertted into a vector, such as a phage or a plasmid to prepare a cDNA library. From the library, a recombinant phage or a recombinant plasmid which has cDNA coding for VH, and a recombinant phage or a recombinant plasmid which has cDNA coding for VL are isolated using as a probe C region portion or V region portion of an antibody of nonhuman animals such as mouse. The full nucleotide sequences of VH and VL of the desired antibody on the recombinant phage or the recombinant plasmid are determined, and the whole amino acid sequences of VH and VL are deduced from the nucleotide sequence.

(3) Construction of an Expression Vector for Human Chimeric Antibodies

An expression vector for human chimeric antibody can be constructed by inserting cDNA coding for VH and VL of a nonhuman animal antibody into a region upstream of the gene coding for CH and CL of the human antibody on the expression vector for humanized antibody obtained in the above 2 (1). For example, an expression vector for human chimeric antibodies can be constructed by preliminarily providing a restriction enzyme recognition site for cloning cDNA coding for VH and VL of a nonhuman animal antibody in a region upstream of a gene coding for CH and CL of the human antibody in the expression vector for chimeric antibodies, and then by inserting cDNA coding for a V region of a nonhuman animal antibody at this cloning site via the synthetic DNA mentioned below. The synthetic DNA consists of a nucleotide sequence at the 3' terminal end of the V region of a nonhuman animal antibody and a nucleotide sequence at the 5' terminal end of the C region of a human antibody, and is produced using a DNA synthesizer so as to have an appropriate restriction enzyme site at both ends thereof.

(4) Identification of CDR Sequence of a Nonhuman Animal Antibody

VH and VL, which form an antigen binding site of an antibody, consist of four framework regions (hereinafter referred to as FR regions) having the sequences relatively conserved, and three complementary determining regions (CDRs) having varied sequences connecting the FR regions [Sequences of Proteins of Immunological Interest, US Dept. Health and Human Services, (1991); hereinafter referred to as Sequences of Proteins of Immunological Interest]. Each CDR amino acid sequence (CDR sequence) can be identified by comparing the amino acid sequences of the V region of the known antibodies (Sequences of Proteins of Immunological Interest).

(5) Construction of cDNA Coding for V Region of Human CDR Grafted Antibodies cDNA coding for VH and VL of a human CDR grafted antibody can be obtained as follows.

In the first step, the amino acid sequence of FRs in a V region of a human antibody is selected with respect to VH and VL, respectively, in order to graft the CDRs of the V region of the desired antibody of a nonhuman antibody. As amino acid sequences of FRs in the V region of a human antibody, any amino acid sequence of FRs in the V region derived from a human antibody can be used. For example, amino acid sequences of FRs in V region of human antibody registered by Protein Data Bank, a common amino acid sequence of each subgroups of the FRs in V region of human antibody (Sequences of Proteins of Immunological Interest) or the like can be used. Among them, the sequence preferably has a high homology to the amino acid sequence of the V region of the desired antibody of nonhuman animals, and more preferably a homology not less than 65%. In the second step, a DNA sequence coding for the selected amino acid sequence of FR in V region of human antibody is ligated to a DNA sequence coding for amino acid sequences of CDRs in V region of a nonhuman animal antibody, and a DNA sequence coding for the amino acid sequence of each VH and VL is designed. In order to obtain a DNA sequence designed to construct gene coding for a CDR grafted antibody variable region, several synthetic DNAs are designed so as to cover the full DNA sequence, with respect to each chain, and thereby a polymerase chain reaction (hereinafter referred to as PCR) is preformed. Taking into consideration the reaction efficiency of PCR and the DNA length capable of being synthesized, preferably six synthetic DNAs are designed. After the reaction, the amplified fragments are subcloned in appropriate vectors, the nucleotide sequence thereof is determined, and a plasmid is obtained which contains cDNA coding for the amino acid sequence of the V region of each chain of the desired human CDR grafted antibody. Alternatively, cDNA coding for the amino acid sequence of the V region of each chain of the desired human CDR grafted antibody can be constructed by synthesizing the full sequence including sense and antisense sequences using synthetic DNA consisting of approximately 100 bases, and annealing and connecting them.

(6) Modification of an Amino Acid Sequence of V Region of a Human CDR Grafted Antibody It is known that when only the CDRs in the V region of the desired nonhuman animal antibody is simply grafted between FRs in V region of a human antibody, the activity of the obtained human CDR grafted antibody is lowered compared to that of the original nonhuman animal antibody [Bio/Technology, 9, 266 (1991)]. Therefore, among the amino acid sequence of FRs in the V region of a human antibody, amino acid residues which are involved in the binding to an antigen, amino acid residues which interact with an amino acid residue in CDR, or amino acid residues which are possibly involved in the preservation of the stereochemical structure of the antibody, are modified to amino acid residues of the original antibody, and thereby increasing the activity thereof. In addition, for the effective indentification of these amino acid residues, construction and analysis of stereochemical structure of the antibody using X-ray crystallographic analysis, computer modeling, or the like are conducted. However, trial and error is necessary with respect to each antibody at present, since a method for producing the human CDR grafted antibody which is applicable to any antibody has not been established yet.

The selected modification of the amino acid sequence of FRs in a V region of human antibody can be achieved using various mutation-introducing primers by performing PCR described in the above section 2(5). Amplified fragments obtained by the PCR are subcloned in appropriate vectors, subsequently the nucleotide sequences thereof are determined to obtain a vector (hereinafter referred to as amino acid sequence modified vector) containing cDNA in which a mutation of interest is introduced.

Alternatively, the modification of an amino acid sequence in a narrow region may be accomplished by PCR-mutagenesis method using primers for mutation consisting of 20–35 bases. More specifically, a sense mutation primer and an antisense mutation primer which consist of 20–35 bases and which contain DNA sequence coding for an amino acid residue to be modified are synthesized, and used to perform two step PCR using as a template a plasmid containing cDNA coding for amino acid sequence of V region which is to be modified. The finally amplified fragments are subcloned in appropriate vectors, the nucleotide sequences thereof are determined, and the amino acid sequence modified vector containing cDNA into which a mutation of interest has been introduced is obtained.

(7) Construction of Expression Vector for Human CDR Grafted Antibodies

An expression vector for human CDR grafted antibody can be constructed by inserting cDNA coding for the VH and VL of a human CDR grafted antibody obtained in the above sections 2(5) and 2(6), into a region upstream of the gene coding for the CH and CL of the human antibody on the expression vector for humanized antibody obtained in the above section 2(1). For example, a recognition site by an appropriate restriction enzyme is introduced to the terminals of the synthetic DNAs at the 5' terminal and 3' terminal for PCR for constructing cDNA coding for the amino acid sequence of VH and VL of human CDR grafted antibody, consequently the DNA being inserted in a region upstream of a desired gene coding for the C region of a human antibody so as to be expressed in the appropriate form.

(8) Transient Expression of Humanized Antibodies and the Evaluation of the Activities Thereof In order to efficiently evaluate the activities of various humanized antibodies, the expression vectors for the human chimeric antibodies of the above section 2(3), the expression vectors for the human CDR grafted antibodies of the above section 2(7), or the modified vectors thereof are treansfected into COS-7 cells (ATCC CRL1651), allowing the transient expression of the humanized antibody [Methods in Nucleic Acids Res., CRC Press, p.283, 1991], and thereby the activities thereof can be determined.

As the method for transfecting expression vectors into COS-7 cells, the DEAE-dextran method [Methods in Nucleic Acids Res., CRC Press, p.283, 1991], the lipofection method [Proc. Natl. Acad. Sci., 84, 7413 (1987)], or the like can be mentioned.

After the transfection of the vector, the activity of the humanized antibody in the culture supernatant can be determined by enzyme-linked immunosorbent assay method (ELISA) described in the above section 1(4) or the like.

(9) Stable Expression of Humanized Antibodies and the Evaluation of the Activities Thereof A transformant which stably produces the humanized antibody can be obtained by transfecting the expression vector of the human chimeric antibody of the above section 2(3) or the expression vector of the human CDR grafted antibody of the above section 2(7) into an appropriate host cell.

As the method for transfecting an expression vector into a host cell, the electroporation method [Japanese Unexamined Patent Application, First Publication No. Hei 2-257891, Cytotechnology, 3, 133 (1990)] or the like can be mentioned.

As a host cell for transfecting an expression vector of a humanized antibody, any host cells which can express the humanized antibody can be used. Examples thereof include mouse SP2/0-Ag14 cell (ATCC CRL1581), mouse P3X63-Ag8.653 cell (ATCC CRL1580), CHO Cell [Proc. Natl. Acad. Sci., 77, 4216 (1980)] in a defect of a dihydrofolate reductase gene (hereinafter referred to as DHFR gene), rat YB2/3HL.P2.G11.16Ag.20 cell (ATCC CRL 1662, hereinafter referred to as YB2/0 cell), or the like.

After the transfection of a vector, a transformant which stably produces a humanized antibody is selected using PRMI1640 medium containing G418 and FCS, according to the method disclosed in Japanese Unexamined Patent Application, First Publication No. Hei 2-257891. The humanized antibody can be produced and accumulated in the culture medium by culturing the obtained transformant in a medium. The activity of the humanized antibody in the culture medium is determined by the method as described in the above section 1(4) or the like. The productivity of the humanized antibody of the transformant can be raised using DHFR gene amplification system and the like, according to the method disclosed in Japanese Unexamined Patent Application, First Publication No. Hei 2-257891.

The humanized antibody can be purified from the culture supernatant of the transformant using a protein A column (Antibodies, Chapter 8). Any other conventional methods for protein purification can be used. For example, the purification can be carried out by the combination of gel filtration, ion-exchange chromatography, ultrafiltration, and the like. The molecular weight of the H chain, L chain, or the whole antibody molecule of the purified humanized antibody can be determined by polyacrylamide gel electrophoresis (SDS-PAGE) [Nature, 21, 680 (1970)], Western blotting method (Antibodies, Chapter 12), or the like.

The reactivity or the binding activity for hTERT of the purified humanized antibody can be determined by the method described in the above section 1(4) and the like.

3. Method for Preparation of Recombinant Antibodies (II)

(1) Method for Preparation of Antibody Fragments Fab, Fab', and F(ab')$_2$

An antibody fragment is formed by treating the above antibody with an enzyme. Examples of the enzymes include papain, trypsin, or the like.

Alternatively, Fab, Fab', or F(ab')$_2$ can be produced by inserting a DNA coding for the Fab, Fab', or F(ab')$_2$ fragment of the anti-human hTERT antibody into an expression vector for animal cells, transfecting the vector into an animal cell, and thereby causing expression of the DNA.

The purification of the obtained antibody fragment can be carried out by the combination of gel filtration, ion-exchange chromatography, affinity chromatography, ultrafiltration, or the like. The molecular weight of the purified Fab, Fab', or F(ab')$_2$ can be determined by polyacrylamide gel electrophoresis (SDS-PAGE) [Nature, 227, 680 (1970)], the Western blotting method (Antibodies, Chapter 12), or the like.

The reactivity or the binding activity for hTERT of the purified Fab, Fab', or F(ab')$_2$ can be determined by the method described in the above section 1(4) or the like.

(2) Method for Preparing Anti-human hTERT Single Chain Antibody

An expression vector for a single chain antibody of a nonhuman animal antibody or for a single chain antibody of human CDR grafted antibody can be constructed, by inserting cDNA coding for the VH and VL of an antibody of a nonhuman animal or a human CDR grafted antibody which are described in the above sections 2(2), 2(5) and 2(6) into a vector for expression of a single chain antibody. As the vector for expressing a single chain antibody employed here, any vector can be used which can incorporate and express cDNA coding for the VH and VL of an antibody of a nonhuman animal or human CDR grafted antibody.

For example, pAGE107 [Cytotechnology, 33, 133(1990)], pAGE103[J. Biochem. 101, 1307(1987)], pHSG274 [Gene, 27, 223 (1984)], pKCR [Proc. Natl. Acad. Sci. U.S.A., 78, 1527 (1981)], pSG1 β d2-4 [Cytotechnology, 4, 173(1990)] or the like can be mentioned. As a host for expressing a single chain antibody can be selected from the group of *Escherichia coli*, yeast, animal cells, or the like; here, the expression vector which is suitable for each host should be selected. Alternatively, a single chain antibody can be secreted outside of the cell, transported in the periplasmic region, or maintained within the cell, by the insertion of cDNA coding for an appropriate signal peptide.

The single chain antibody expression vector, in which cDNA coding for the desired single chain antibody is inserted, can be constructed by inserting a cDNA coding for a single chain antibody consisting of VH-L-VL or VL-L-VH (L is a peptide linker) into the selected expression vector in a region downstream of an appropriate promoter and signal peptide.

The cDNA coding for a single chain antibody can be obtained by linking cDNA coding for VH and cDNA coding for VL, using synthetic DNA coding for peptide linker with recognition sites by an appropriate restriction enzyme on both of its sides. It is important that the linker peptide is optimized so that the addition of the linker peptide does not interfere with the binding of VH and VL to an antigen. Examples of these include the one shown by Pantoliano et al. [Biochemistry, 30, 10117(1991)] or one modified therefrom.

(3) Method for Preparing Anti Human hTERT Disulfide Stabilized Antibody

The DNA sequence which corresponds to one amino acid residue at a suitable position of the cDNA coding for the VH and VL of a nonhuman antibody, or of the cDNA coding for the VH and VL of a human CDR grafted antibody is modified into the DNA sequence which corresponds to cysteine residue; the modified cDNA is expressed and purified; then a disulfide bond is formed; a disulfide stabilized antibody can be prepared. The modification of an amino acid residue into a cysteine residue can be carried out by the mutagenesis method using the PCR of the above section 2(5).

An expression vector for a disulfide stabilized antibody H chain or an expression vector for a disulfide stabilized antibody L chain can be constructed by inserting cDNA coding for the obtained modified VH and modified VL into an appropriate expression vector.

As expression vector for disulfide stabilized antibody used here, any expression vectors are available which can incorporate and express cDNA coding for modified VH and modified VL. Examples thereof include pAGE107 [Cytotechnology, 33, 133(1990)], pAGE103[J. Biochem. 101, 1307(1987)], pHSG274 [Gene, 27, 223 (1984)], pKCR [Proc. Natl. Acad. Sci. U.S.A., 78, 1527 (1981)], pSG1 β d2-4 [Cytotechnology, 4, 173(1990)] or the like. As a host for expressing an expression vector of disulfide stabilized antibody H chain and an expression vector of disulfide stabilized antibody L chain to form a disulfide stabilized antibody, an appropriate one can be selected from the group of *Escherichia coli*, yeast, animal cells, and the like; here, the expression vector which is suitable for each host should be selected.

Alternatively, a disulfide stabilized antibody can be secreted outside of the cell, transported to the periplasmic region, or maintained within the cell, by the insertion of cDNA coding for an appropriate signal peptide.

(4) Expression and Evaluation for Activities of Various Antibodies

A transformant which produces an antibody fragment, single chain antibody, disulfide stabilized antibody H chain, or disulfide stabilized antibody L chain of interest can be obtained, by transfecting the expression vector for the antibody fragment, the expression vector for the single chain antibody, the expression vector for disulfide stabilized antibody H chain, or the expression vector for disulfide stabilized antibody L chain, into a host cell, using the electroporation method [Japanese Unexamined Patent Application, First Publication No. Hei 2-257891; Cytotechnology, 3, 133 (1990)] or the like. After transfection of the expression vector, the expression of the antibody fragment, the single chain antibody, the disulfide stabilized antibody H chain, or the disulfide stabilized antibody H chain can be confirmed according to the method described in the above section 1(4) or the like.

The collection and purification of the antibody fragment the single chain antibody, the disulfide stabilized antibody L chain, or the disulfide stabilized antibody H chain can be achieved by the combination of known techniques. For example, when the antibody fragment, the single chain antibody, the disulfide stabilized antibody H chain, or the disulfide stabilized antibody L chain is secreted into a medium, the collection and purification can be achieved by concentrating by ultrafiltration, and successively by conducting various chromatography or gel filtaration operations. When it is transported to the periplasma region of a host cell, the collection and purification can be achieved by loading the shock of osmotic pressure on the cell and performing ultrafiltration, and successively by conducting various chromatography or gel filtaration. When the antibody fragment, the single chain antibody, the disulfide stabilized antibody H chain, or the disulfide stabilized antibody L chain is insoluble and exists as a inclusion body, the collection and purification can be achieved by cytolysis and repeated centrifugation and washing to isolate the inclusion body, for example, solubilization by guanidine-hydrochloric acid, and successively by conducting various chromatography or gel filtaration operations.

The purified single chain antibody can be determined by the method described in the above section 1(4) or the like.

The purified disulfide stabilized antibody H chain and the disulfide stabilized antibody L chain are mixed, and subjected to a refolding procedure for deriving an active structure [refolding operation; Molecular Immunology, 32, 249 (1995)] to form a disulfide bond, followed by antigen-affinity chromatography or ion exchange chromatography or gel filtaration is conducted, and thereby the active disulfide stabilized antibody can be purified. The activity of the disulfide stabilized antibody can be determined by the method described in the above section 1(4) and the like.

4. Method for the Preparation of a Fusion Antibody

A fusion antibody, in which an antibody or antibody fragment thereof used in the present invention is bound to a radioactive isotope, a protein, or a low molecular agent by chemical or genetic engineering method, can be used as a derivative of an antibody.

A fusion antibody in which an antibody and toxic protein are chemically bound can be prepared by the method described in the literatures [Anticancer Research, 11, 2003 (1991); Nature Medicine, 3, 350 (1996)].

A fusion antibody in which an antibody and a toxin or a protein such as cytokine are linked by a genetic engineering method can be prepared according to the method described in the literatures [Proceeding of National Academy of Science USA, 93, 974 (1996); Proceeding of National Academy of Science USA, 93, 7826 (1996)].

A fusion antibody in which an antibody and a low molecular weight anticancer agent are chemically bound can be prepared by the method described in the literature [Science, 26, 212 (1993)].

A fusion antibody in which an antibody and a radioactive isotope are chemically bound can be prepared by the method described in the literatures [Antibody Immunoconjugates and Radiopharmaceuticals, 3, 60 (1990); Anticancer Research, 11, 2003 (1991)].

It is expected that these derivatives can provide more effective and side effect-reduced diagnoses and treatments by accumulating a radioactive isotope, a protein (such as cytokine, a toxin or an enzyme) or a low molecular agent within the peripheral of a target tissue, based on the specificity of antibody molecules.

5. Method for Using the Antibody (I)

It is believed that the above-described anti-hTERT antibodies, the antibody fragments thereof, or the antibodies thereof fused with the other molecules are useful for treatment of cancers such as lung cancer, colon cancer, breast cancer, inflammatory diseases, and allergic diseases, since these antibodies bind to human hTERT and destroy cells expressing hTERT on the cell surface through effector activities of antibodies such as ADCC, CDC, or the like.

The pharmaceutical preparation containing the antibody of the present invention can be administered alone as therapeutic agents; however, it is usually preferred that they are mixed with at least one pharmacological acceptable carriers for pharmaceutical preparation in accordance with conventional methods which are well known in the art of pharmaceuticals.

It is preferred to select an administration route which is the most effective route for the treatment. For example, oral administration; or parenteral administration such as intraoral, tracheobronchial, rectal, subcutaneous, intramuscular, or intravenous administration are mentioned. In the case of antibody preparations, intravenous administration is preferred.

The dosage form includes nebulas, capsules, tablets, granules, syrups, emulsions, suppositories, injections, ointments, and tapes.

Examples of the pharmaceutical preparations suitable for oral administration include emulsions, syrups, capsules, tablets, powders, and granules preparations.

Liquid preparation such as emulsions and syrups can be prepared using water; sugars such as sucrose, sorbitol, and fructose; glycols such as polyethylene glycol and propylene glycol; oils such as sesami oil, olive oil, and soybean oil; preservatives such as p-hydroxybenzoic esters; flavors such as strawberry flavor and peppermint, as additives.

Capsules, tablets, powders, granules, or the like can be prepared using excipients such as lactose, glucose, sucrose, and mannitol; disintegrators such as starch and sodium alginate; lubricants such as magnesium stearate and talc; binders such as polyvinyl alcohol, hydroxypropyl cellulose, gelatin; detergents such as fatty acid esters; plasticizers such as glycerin, as additives.

Examples of pharmaceutical preparations suitable for parenteral administration include injections, nebulas, and suppositories.

Injections can be prepared using carriers such as salts solution, glucose solution, or mixtures thereof.

Suppositories can be prepared using carriers such as cacao butter, hydrogenated fat, or carboxylic acid, or the like.

Nebulas can be prepared by using the compound itself, or by using carriers or the like which disperse the compound in the form of fine particles and facilitate absorption thereof without irritating tunica mucosa of oral cavity and airway of recipients.

Examples of the carriers include lactose, glycerin, or the like. Other preparations such as aerosol and dry powder can be prepared depending on the properties of the compound and the used carriers. In addition, in these parenteral preparations, the additives which are exemplified in the oral preparations can be also added.

The dose and administration schedule may vary depending on the desired effect of the treatment, administration route, the period of the treatment, age, body weight, or the like, however, the dose is generally 10 $\mu$g/kg~8 mg/kg a day for adult.

The antibodies for human hTERT of the present invention efficiently react with cells derived from patients suffering from cancers such as lung cancer, colon cancer, breast cancer, inflammatory diseases, or allergic diseases, and therefore can be used for diagnosis agents or therapeutic agents for these diseases.

As the method for examining the anti-tumor effects of the antibodies of the present invention against various tumor cells, in vitro examination such as measurements of complement-dependent cytotoxicity (CDC activity), antibody dependent cellular cytotoxicity (ADCC activity), or the like, and in vivo examinations such as anti-tumor examination using a tumor system in experimental animals such as mice or the like can be mentioned.

The CDC activity, ADCC activity, and anti-tumor examination can be carried out according to methods described in the literatures [Cancer Immunology Immunotherapy, 36, 373, 1993, Cancer Reseach, 54, 1511 (1994)] or the like.

6. Method for Using the Antibody (II)

In addition, the present invention relates to a method for immunologically detecting and assaying the telomerase catalytic subunit hTERT; and microorganisms, animal cells, or insect cells expressing intracellularly or extracellularly the telomerase catalytic subunit hTERT, using the monoclonal antibodies of the present invention.

As a method for immunologically detecting and assaying the telomerase catalytic subunit hTERT; and microorganisms, animal cells, or insect cells expressing intracellularly or extracellularly telomerase catalytic subunit hTERT, the fluorescent antibody method, the enzyme-linked immunosorbent assay method (ELISA), radioimmunoassay (RIA), immunohistochemical staining methods (ABC method, CSA method, and the like) such as immunohisto staining methods and immunocyte staining methods, the Western blotting method, the dot blotting method, the immune precipitation method, the above-mentioned enzyme-linked immunosorbent assay method, the sandwich ELISA method (Monoclonal Antibody Experiment Manual (Kodansha Scientific, 1987), Biochemical Experiments Lecture Series 5, Immuno-Biochemistry Research Methods (Tokyo Kagaku Dojin, 1986)) and the like can be mentioned.

The fluorescent antibody method is the method wherein telomerase catalytic subunit hTERT, or microorganisms, animal cells, or insect cells expressing intracellularly or extracellularly the telomerase catalytic subunit hTERT are reacted with the monoclonal antibody of the present invention; and further reacted with an anti-mouse-IgG antibody or binding fragment labeled with a fluorescent compound such as fluorescein-isothiocyanate (FITC); and the fluorescent dye is measured by a flow cytometer.

The enzyme-linked immunosorbent assay method (ELISA) is the method wherein telomerase catalytic subunit hTERT, or microorganisms, animal cells, or insect cells expressing intracellularly or extracellularly the telomerase catalytic subunit hTERT are reacted with the monoclonal antibody of the present intention; and further reacted with an anti-mouse-IgG antibody or binding fragment labeled with a enzyme such as peroxidase, biotin or the like; and the coloring dye is measured by an absorbance meter.

The radioimmunoassay (RIA) is the method wherein telomerase catalytic subunit hTERT, or microorganisms, animal cells, or insect cells expressing intracellularly or extracellularly the telomerase catalytic subunit hTERT are reacted with the monoclonal antibody of the present intention; further reacted with an anti-mouse-IgG antibody or binding fragment labeled with a ratioisotope; and measured by a scintillation counter or the like.

The immunohisto staining methods and immunocyte staining methods are the methods wherein telomerase catalytic subunit hTERT, or microorganisms, animal cells, or insect cells expressing intracellularly or extracellularly the telomerase catalytic subunit hTERT are reacted with the monoclonal antibody of the present invention; further reacted with anti-mouse-IgG antibody or binding fragment labeled with a fluorescent compound such as FITC or the like or with a enzyme such as peroxidase, biotin, or the like; and observed under a microscope.

The Western blotting method is the method wherein telomerase catalytic subunit hTERT, or a cell extract of microorganisms, animal cells, or insect cells expressing intracellularly or extracellularly the telomerase catalytic subunit hTERT are fractionated by SDS-polyacrylamide gel electrophoresis [Antibodies-A Laboratory Manual, Cold Spring Harbor Laboratory, 1988]; the gel is blotted to PVDF membrane or nitrocellulose membrane; and the membrane is reacted with the monoclonal antibody of the present invention, further reacted with an anti-mouse-IgG antibody or binding fragment labeled with a fluorescent compound such as FITC or with an enzyme such as peroxidase, biotin, or the like, and confirmed.

The Dot blotting method is the method wherein telomerase catalytic subunit hTERT, or a cell extract of microorganisms, animal cells, or insect cells expressing intracellularly or extracellularly the telomerase catalytic subunit hTERT are blotted to nitrocellulose membrane; and the membrane is reacted with the monoclonal antibody of the present invention, further reacted with an anti-mouse-IgG antibody or binding fragment labeled with a fluorescent compound such as FITC or with an enzyme such as peroxidase, biotin, or the like, and confirmed.

The immuno-precipitation method is the method wherein telomerase catalytic subunit hTERT, or microorganisms, animal cells, or a cell extract of insect cells expressing intracellularly or extracellularly the telomerase catalytic subunit hTERT are reacted with the monoclonal antibody of the present invention; and antigen-antibody complex is precipitated by adding a carrier, such as protein G-Sepharose, having a specific binding activity with immunoglobulin.

The sandwich ELISA method is conducted as follows. Among two monoclonal antibodies having different antigen recognition sites, one of the monoclonal antibodies is adsorbed onto a plate, and the other monoclonal antibody is labeled with a fluorescent compound such as FITC or with a enzyme such as peroxidase or biotin. Then, the antibody-adsorbed plate is reacted with telomerase catalytic subunit hTERT, or a cell extract of a microorganism, animal cells, or insect cells expressing intracellularly or extracellularly the telomerase catalytic subunit hTERT, and reacted with the labeled monoclonal antibody; and the reaction corresponding to the labeling compound is carried out.

As the diagnosis method of a disease in which telomerase is involved, the method for immunologically detecting and quantitating telomerase catalytic subunit hTERT using various human tumor culture cell or a cell collected from patients by biopsy and the like and the cell extract prepared from the cells, as described above can be mentioned. As a disease in which telomerase is involved, cancer or the like can be mentioned.

The monoclonal antibody of the present invention can be used as a diagnosis for these diseases.

7. Method for Using Antibodies (III)

In addition, the anti-hTERT monoclonal antibody of the present invention can be used for purifying telomerase catalytic subunit hTERT. In more detail, the affinity chromatography using the antibody of the present invention is carried out. The anti-hTERT monoclonal antibody is immobilized to a carrier by using a carrier, such as protein G-Sepharose, which has a specific binding activity with immunoglobulin, or using various coupling gels directly binding to immunoglubulin through an amino group, and thereby an antibody column is prepared.

As a sample, cell extracts of animal cells or insect cells which express hTERT, various human tumor culture cells, or cell extracts prepared from a cell collected from patients by biopsy or the like can be used.

The above-mentioned hTERT sample is passed through the antibody column, and the column is washed by phosphate buffer (pH 7.2) containing 0.5M NaCl in a volume of 10 times as much as the column volume. Then, the purified hTERT is obtained by the elution with a buffer under conditions where the antigen-antibody reaction dissociates (high pH, low pH, high salt content, detergent, denaturant, or the like). It is necessary that the elution is conducted under conditions in which the enzyme activity of hTERT is not inactivated.

BRIEF DESCRIPTION OF DRAWINGS

FIG. 9 is a chart showing the results of the detection of hTERT protein present within cells by cytological staining using the monoclonal antibodies of the present invention.

BEST MODE FOR CARRYING OUT THE INVENTION

Figure 1:
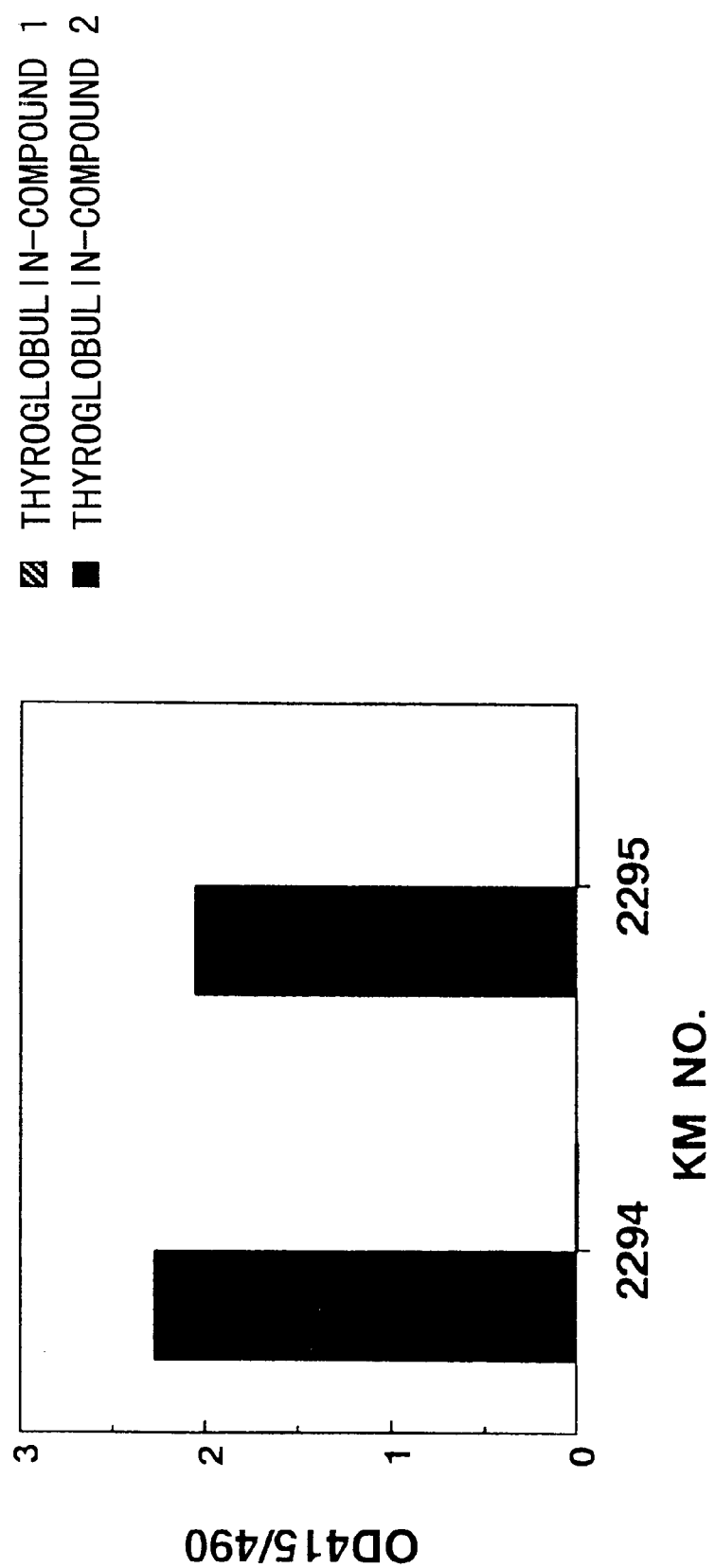
FIG. 1 is a graph showing the results of reactivity for Compounds 1 and 2 of the monoclonal antibodies of the present invention obtained using Compound 2 as an antigen, by enzyme-linked immunosorbent assay.

The following is the more detailed explanation of the present invention, illustrated by Examples. It goes without saying that the present invention is not limited by these Examples.

EXAMPLE 1

Preparation of the Anti-hTERT Monoclonal Antibody (1)

(1) Preparation of Antigen

The hTERT protein sequence was analyzed using Genetyx Mac, and a partial peptide of 1–17 from the N-terminal of the human telomerase catalytic subunit (Compound 2, SEQ ID NO: 1), a partial peptide of 642–661 from the N-terminal of the human telomerase catalytic subunit (Compound 1 SEQ ID NO: 2), and a partial peptide of 1177–1192 from the N-terminal of the human telomerase catalytic subunit (Compound 3, SEQ ID NO: 3) were selected from the highly hydrophilic sections, the N-terminal and the C-terminal, as partial sequences considered to be suitable as antigens.

Codes

The code for the amino acids and the protective groups thereof which are used in the present invention are in accordance with the recommendations of the IUPAC—IUB Joint Commission on Biochemical Nomenclature [European Journal of Biochemistry, Vol. 138, Page 9, (1984)].

The following codes represent the following amino acids except where specifically indicated otherwise.
Ala: L-alanine
Arg: L-arginine
Asn: L-asparagin
Asp: L-aspartic acid
Asx: L-aspartic acid or L-asparagin
Cys: L-cysteine
Glu: L-glutamic acid
Glx: L-glutamic acid or L-glutamine
Gly: L-glycine
Ile: L-isoleucine
Leu: L-leucine
Lys: L-lysine
Met: L-methionine
Phe: L-phenylalanine
Pro: L-proline
Ser: L-serine
Thr: L-threonine
Val: L-valine The following codes represent the side chain protective amino acids and protective groups of the following corresponding amino acids.
Ac: acetyl
Fmoc: 9-fluororenylmethyloxycarbonyl
t-Bu: t-butyl
Trt: trityl
Pmc: 2,2,5,7,8-pentamethylchroman-6-sulfonyl
Boc: t-butyloxycarbonyl
Fmoc-Thr(t-Bu)-OH: Nα-9-fluororenylmethylox carbonyl-O-t-butyl-L-threonine
Fmoc-Ser(t-Bu)-OH: Nα-9-fluororenylmethyloxycarbonyl-O-t-butyl-L-serine
Fmoc-Lys(Boc)-OH: Nα-9-fluororenylmethyloxycarbonyl-Nε-t-butyl-oxycarbonyl-L-lysine
Fmoc-Asn(Trt)-OH: Nα-9-fluororenylmethyloxycarbonyl-Nγ-trityl-L-asparagine
Fmoc-Asp(O-t-Bu)-OH: Nα-9-fluororenylmethyloxycarbonyl-L-aspartic acid-β-t-butylester
Fmoc-Glu(O-t-Bu)-OH: Nα-9-fluororenylmethyloxycarbonyl-L-glutamic acid-γ-t-butylester
Fmoc-Arg(Pmc)-OH: Nα-9-fluororenylmethyloxycarbonyl-Ng-2,2,5,7,8-pentamethylchroman-6-sulfonyl-L-arginine
Fmoc-Cys-(Trt)-OH: Nα-9-fluororenylmethyloxycarbonyl-S-trityl-L-cysteine The following codes represent the following corresponding reaction solvents, reaction systems and the like.
HBTU: 2-(1H-benzotriazol-1-yl)-1,1,3,3-tetramethyleuronium/hexsafluorophosphate
HOBt: N-hydroxybenzotriazol
DMF: N,N-dimethylformamide
DCM: dichloromethane
TFA: trifluoroacetic acid
DIEA: diisopropylethylamine ① Compound 1 (SEQ ID NO: 2) Synthesis of (Ac-Ala-Arg-Thr-Phe-Arg-Arg-Glu-Lys-Arg-Ala-Glu-Arg-Leu-Thr-Ser-Arg-Val-Lys-Ala-Cys-OH).

30 mg of carrier resinchlorotrityl resin manufactured by AnaSpec) bonded to 14.1 μmol of H-Cys(Trt) was put into the reaction chamber of an automatic synthesizer (Shimadzu Seisakusho), 1 ml DCM/DMF (1:1) were added, stirred for 10 minutes and the solution discharged. In addition, 1 ml of DMF was added, stirred for 1 minute andthe solution discharged, then the following operations were carried out in accordance with the program for synthesis of the Shimadzu Seisakusho.

(a) Fmoc-Ala-OH (141 μmol), HBTU (141 μmol), hydrate of HOBt1 (141 μmol) and DIEA (282 μmol) in DMF (734 μl) were stirred for 3 minutes, and the obtained solution was added to resin and the mixture was stirred for 30 minutes, and then the solution discharged.

(b) The carrier resin was washed for 1 minute with 734 μl of DMF and this was repeated five times. In this way, Fmoc-Ala-Cys(Trt) was synthesized on the carrier.

Next the following Fmoc group protection removal process was conducted.

(c) 734 μl of 30% piperidine—DMF solution was added and the mixture stirred for four minutes, this solution was then discharged and this operation was repeated once.

(d) The carrier resin was washed for 1 minute with 500 μl of DMF, this solution was discharged, and this operation was repeated five times.

In this way, a carrier resin bonded with H-Ala-Cys(Trt) having the Fmoc group removed was obtained.

Next, H-Lys(Boc)-Ala-Cys(Trt) was synthesized on a carrier by conducting a condensation reaction using the Fmoc-Lys(Boc)-OH using the process of (a), and by passing through the washing process of (b), and the protection removal processes of (c) and (d). Next, a carrier resin bound to a side chain protection peptide was obtained by successively using Fmoc-Val-OH, Fmoc-Arg(Pmc)-OH, Fmoc-Ser (t-Bu)-OH, Fmoc-Thr(t-Bu)-OH, Fmoc-Leu-OH, Fmoc-Arg (Pmc)-OH, Fmoc-Glu(Ot-Bu)-OH, Fmoc-Ala-OH, Fmoc-Arg(Pmc)-OH, Fmoc-Lys(Boc)-OH, Fmoc-Glu(Ot-Bu)-OH, Fmoc-Arg(Pmc)-OH, Fmoc-Arg(Pmc)-OH, Fmoc-Phe-OH, Fmoc-Thr(t-Bu)-OH, Fmoc-Arg(Pmc)-OH, Fmoc-Ala-OH, then, after repeating (a)–(d), washing successively with methanol and butylether and drying under reduced pressure for 12 hours. To this, 1 ml of a solution mixture comprising TFA (82.5%), theoanisol (5%), water (5%), ethyl methyl sulfide (3%), 1,2-ethanedithiol (2.5%) and thiophenol (2%) was added and allowed to stand for 8 hours at room temperature, and the side chain protection units were remove while the peptide was separated from the resin. After filtering the resin, approximately 10 ml of ether were added to the obtained solution, the produced precipitate was collected by centrifugation and decantation, and thereby 36.2 mg were collected as crude peptide. After washing this crude product in 2 M acetic acid, it was purified by HPLC using a reverse phase column (CAPCELL PAK C18 30 mml.D.×25 mm, manufactured by Shiseido). The fraction containing Compound 1 was obtained by elution using linear gradient method carried out with the addition of 90% acetonitrile aqueous solution containing 0.1% TFA to a 0.1% TFA aqueous solution, and detection at 220 nm. 2.3 mg of Compound 1 was obtained by freeze drying this fraction.

Mass Spectrography [FABMS]: m/z=2477.4(M+H$^+$);

Amino acid analysis: Glx 2.0 (2), Ser 1.2 (1), Arg 5.4 (6), Thr 2.0 (2), Ala 3.2 (3), Val 1.0 (1), Leu 1.3 (1), Lys 2.0 (2), Phe 0.8 (1), Cys 1.5 (1).

② Compound 2 (SEQ ID NO: 1) Synthesis of (H-Met-Pro-Arg-Ala-Pro-Arg-Ser-Arg-Ala-Val-Arg-Ser-Leu-Leu-Arg-Ser-Cys-OH)

A carrier resin bonded with side chain protective peptides was obtained using 30 mg of a carrier resin (chlorotrityl resin manufactured by AnaSpec) bonded to 14.1 μmol of H-Cys(Trt) as the starting material, in the same way as in Example 1, by successively condensing Fmoc-Ser(t-bu)-OH, Fmoc-Arg(Pmc)-OH, Fmoc-Leu-Oh, Fmoc-Leu-OH, Fmoc-Ser(t-Bu)-OH, Fmoc-Arg(Pmc)-OH, Fmoc-Val-OH, Fmoc-Ala-OH, Fmoc-Arg(Pmc)-OH, Fmoc-Ser(t-Bu)-OH, Fmoc-Arg(Pmc)-OH, Fmoc-Pro-OH, Fmoc-Ala-OH, Fmoc-Arg(Pmc)-OH, Fmoc-Pro-OH, and Fmoc-Met-OH, washing and drying. In the same way as in Compound 1, cleavage of side chain protection groups and separation from the resin were carried out, 31.1 mg of crude peptide was obtained, and purified by HPLC using a reverse phase column, thereby, 4.8 mg of Compound 2, was obtained.

Mass Spectrography [FABMS]: m/z=1956.7 (M+H$^+$);

Amino acid analysis: Ser 3.0 (3), Arg 4.7 (5), Ala 2.0 (2), Pro 2.0 (2), Val 1.0 (1), Leu 2.3 (2), met 1.0 (1), Cys 1.4 (1).

③ Compound 3 (SEQ ID NO: 3) Synthesis of (H-Cys-Ala-Ala-Asn-Pro-Ala-Leu-Pro-Ser-Asp-Phe-Lys-Thr-Ile-Leu-Asp-OH)

A carrier resin bonded with side chain protective peptides was obtained using 30 mg of a carrier resin (Wang resin manufactured by NovaBioche) bonded to 14.1 μmol of Fmoc-Asp(Ot-Bu) as the starting material, by after carrying out processes (c) and (d) in Compound 1, successively condensing Fmoc-Leu-OH, Fmoc-Ile-OH, Fmoc-Thr(t-Bu)-OH, Fmoc-Lys(Boc)-OH, Fmoc-Phe-OH, Fmoc-Asp(Ot-Bu)-OH, Fmoc-Ser(t-Bu)-OH, Fmoc-Pro-OH, Fmoc-Leu-OH, Fmoc-Ala-OH, Pmoc-Pro-OH, Fmoc-Asn(Trt)-OH, Fmoc-Ala-OH, Fmoc-Ala-OH, Fmoc-Cys(Trt)-OH, washing and drying in the same way as in Compound 1. In the same way as in Compound 1, cleavage of side chain protection groups and separation from the resin were carried out, 27.6 mg of crude peptide was obtained, and purified by HPLC using a reverse phase column, thereby, 10.3 mg of Compound 3 was obtained.

Mass Spectrography [FABMS]: m/z=1675.6 (M+H$^+$);

Amino acid analysis: Glx 3.0 (3), Ser 1.1 (1), Ala 3.0 (3), Pro 2.1 (2), Leu 2.0 (2), Lys 1.0 (1), Ile 0.9 (1), Phe 1.0, Cys 1.0 (1).

(2) Preparation of Immunogen

In order to increase immunogenicity, the hTERT partial peptide obtained in Example 1 (1) was made into a conjugate with KLH (Carbochem Co.) using the following method and used as an immunogen. That is, 10 mg/ml of KLH was prepared by dissolving in PBS, then an amount equivalent to 1/10th of the total volume of 25 mg/ml MBS (Nakaraitesku Co.) was added dropwize and reacted with stirring for 30 minutes. 2.5 mg of KLH-MB obtained by the removal of free MBS using a gel filtration column such as Sephadex G-25 equilibrated with PBS in advance was mixed with 1 mg of peptide dissolved in 0.1 M sodium phosphate buffer (pH 7.0) and reacted while stirring for 3 hours at room temperature. After the reaction, dialysis was conducted with PBS-0.5 M NaCl.

(3) Immunization of Animals and Preparation of Antibody Producing Cells

100 μg of the peptide—KLH conjugate prepared in Example 1 (2) was administered together with 2 mg of aluminum gel and 1×10$^9$ cells of pertussis vaccine (manufactured by Chiba Prefecture Serum Laboratory) to 5 week old female mice (Balb/c), then, two weeks later, 100 μg of conjugate was administered once a week for a total of 4 times. Blood was collected from the venous plexus of the fundus oculi (eyegrounds) and the serum antibody titer was determined by enzyme-linked immunosorbent assay as shown below. Three days after the last immunization, the spleen was excised from mice who showed sufficient antibody titer.

The spleen was cut to pieces in MEM medium (manufactured by Nissui Seiyaku Co.), loosened using tweezers, and centrifuging (1,200 rpm, for 5 minutes), the supernatant discarded, removed red blood cells by treating with Tris-ammonium chloride buffer (pH 7.65) for 1 to 2 minutes, washed with MEM medium 3 times, and used in the cell fusion.

(4) Enzyme-linked Immunosorbent Assays

In the antigen for the assay, one in which the hTERT partial peptide obtained in Example 1 (1) was conjugated with thyroglobulin (hereinafter abbreviated as THY) was used. The preparation method was the same as described in Example 1(2), except that SMCC (Sigma Co.) was used in place of MBS as the cross-linking agent. To a 96 well EIA plate (Griener Co.), 50 μl of the 10 μg/ml conjugate prepared in the above mentioned way was added to each well and allowed to stand over night at 4° C. to adsorb. After washing, 100 μl of 1% BSA-PBS was added to each well, reacted for 1 hour at room temperature, and the remaining active groups blocked. The 1% BSA-PBS was discarded, and 50 μl of antiserum of the mouse to be immunized, culture supernatant of the anti-hTERT monoclonal antibody or purified monoclonal antibodies were added to each well and allowed to react for 2 hours. After washing with tween-PBS, 50 μl of rabbit anti-mouse immunoglobulin labeled with peroxidase (Dako Co.) was added to each well and allowed to react for 1 hour at room temperature, then, after washing with tween-PBS, color was developed using ABTS matrix liquid [2.2-adinobis(3-ethylbenzothiazol-6-sulfonic acid) ammonium] and OD415 nm absorbance was measured using a plate reader (NJ 2001; manufactured by Nihon Intermed Co.).

(5) Preparation of the Mouse Myeloma Cells 8-azaguanine resistant mouse bone marrow tumor cell line P3-U1 was cultured in normal medium, more than 2×10$^7$ cells were obtained at the time of cell fusion, and submitted as a parental strain in the cell fusion.

(6) Preparation of Hybridoma

Mouse spleen cells obtained in Example 1(3) and bone marrow tumor cells obtained in (5) were mixed so as to be 10:1, after centrifugation (1,200 rpm, for 5 minutes), the supernatant was discarded, and the precipitated cells were well loosened, then, while stirring, 0.2–1 ml of a liquid mixture of 2 grams of polyethylene glycol—1000 (PEG-1,000), 2 ml of MEM medium, and 0.7 ml of dimethylsulfoxide was added per 108 mouse spleen cells, and then after adding 1–2 ml of MEM medium several times every for 1–2 minutes, MEM medium was added so as to give a total amount of 50 ml. After centrifugation (900 rpm, for 5 minutes), the supernatant was discarded, cells were made loose, then the loosened cells were suspended in 100 ml of HAT medium by being drawn up into a measuring pipette and then discharged.

100 μl of this suspension were added to each well of a 96 well culturing plate, and cultured under 5% $CO_2$ for 10–14 days at 37° C. in a 5% $CO_2$ incubator. The supernatant of this culture was tested using the enzyme-linked immunosorbent assay described in Example 1 (4), wells which reacted with the hTERT partial peptide and did not react with the control peptide were selected, and, changing the HT medium with normal medium, cloning was repeated two times, thereby establishing the anti-hTERT monoclonal antibody producing hybridoma.

Using Compound 2 (SEQ ID NO: 1), 2 monoclonal antibodies, KM2294 and KM 2295 were selected; using Compound 1 (SEQ ID NO: 2), 8 monoclonal antibodies, KM2277, KM2278, KM2279, KM2280, KM2281, KM2282, KM2283 and KM2284 were selected; and using Compound 3 (SEQ ID NO: 3) as the antigen, 17 monoclonal antibodies, KM2296, KM2297, KM2298, KM2299, KM2300, KM2301, KM2302, KM2303, KM2304, KM2305, KM2306, KM2307, KM2308, KM2309, KM2310, KM2311, and KM2312 were selected.

(7) Purification of Monoclonal Antibody

Cells of the hybridoma lines obtained in Example 1 (6) were injected peritoneally into 8 week old, female, nude mice (Balb/c) treated with pristane in an amount of 5~20× $10^6$ cells/animal. 10–21 days later, the hybridoma produced ascitic cancer. Ascites (1–8 ml/animal) was collected from mice in which ascites had accumulated, and the solid portion removed by centrifugation (3,000 rpm, for 5 minutes). When the monoclonal antibodies were IgM, salting out was conducted with 50% ammonium sulfate, and after dialysis with PBS to which 0.5 M of sodium chloride had been added, the IgM fraction was collected by passing through a column of Cellulofine GSL 2000 (Seikagaku Industries KK) (750 ml bed volume) at a rate of 15 ml/hour, to obtain purified monoclonal antibodies. When the monoclonal antibodies were IgG, purified monoclonal antibodies were obtained by purification using caprylic acid precipitation (Antibodies—A Laboratory Manual, Cold Spring Harbor Laboratory, 1988).

The subclass of the antibodies was determined by enzyme-linked immunosorbent assay using a sub-class typing kit (Table 1).

TABLE 1

| KM No. | Antibody Class |
|---|---|
| 2277 | IgG1 |
| 2278 | IgG1 |
| 2279 | IgG1 |
| 2280 | IgG1 |
| 2281 | IgG1 |
| 2282 | IgG1 |
| 2283 | IgG1 |
| 2284 | IgG1 |
| 2294 | Unknown |
| 2295 | IgG1 |
| 2296 | IgG1 |
| 2297 | IgG1 |
| 2298 | IgG1 |
| 2299 | IgG1 |
| 2300 | IgG1 |
| 2301 | IgM |
| 2302 | IgG1 |
| 2303 | IgG1 |
| 2304 | IgM |
| 2305 | Ig2b |
| 2306 | Ig2b |
| 2307 | unknown |
| 2308 | IgG1 |
| 2309 | IgG1 |
| 2310 | IgG1 |
| 2311 | IgG1 |
| 2312 | IgM |

(8) Reactivity With the hTERT Partial Peptide (Enzyme-linked Immunosorbent Assay)

Reactivity of the anti-hTERT monoclonal antibody selected in Example 1 (6) with the investigated using the enzyme-linked immunosorbent assay shown in (4).

Figure 2:
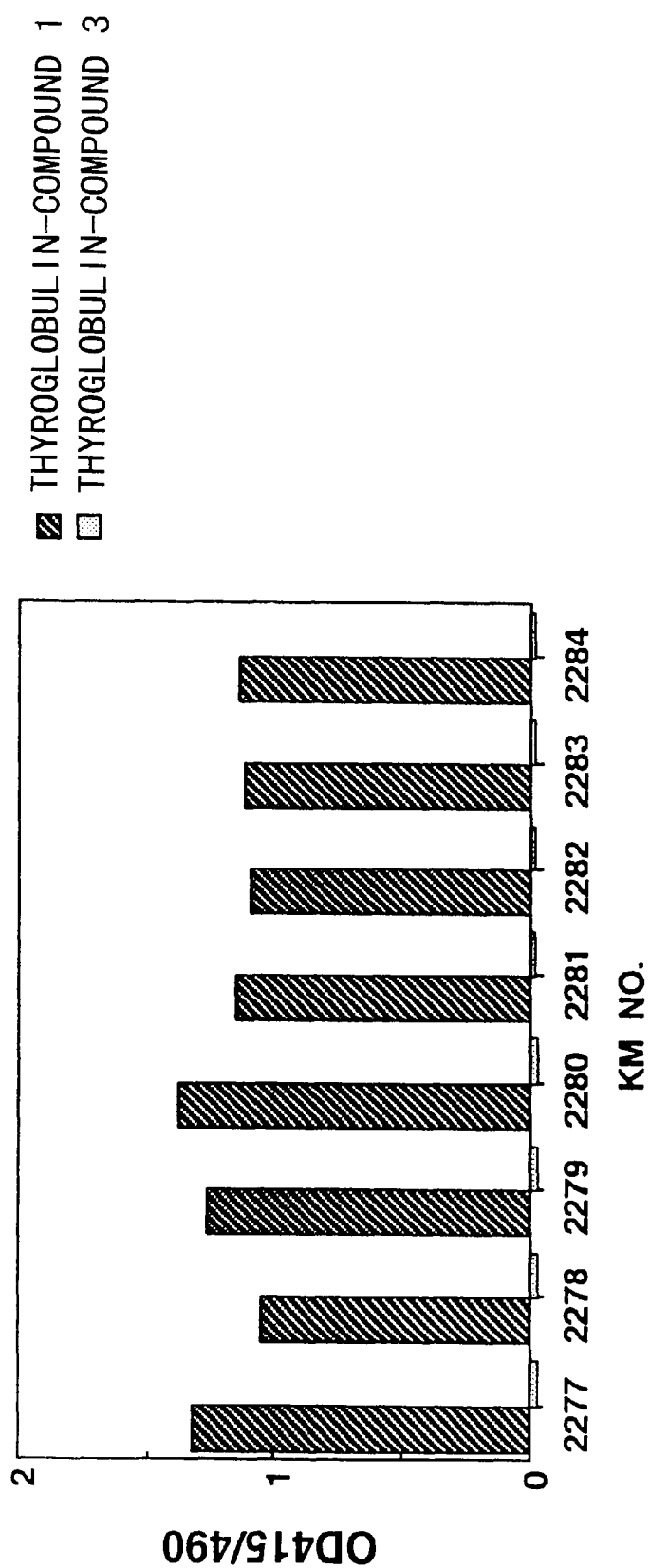
FIG. 2 is a graph showing the results of reactivity for Compounds 1 and 3 of the monoclonal antibodies of the present invention obtained using Compound 1 as an antigen, by enzyme-linked immunosorbent assay.
Figure 3:
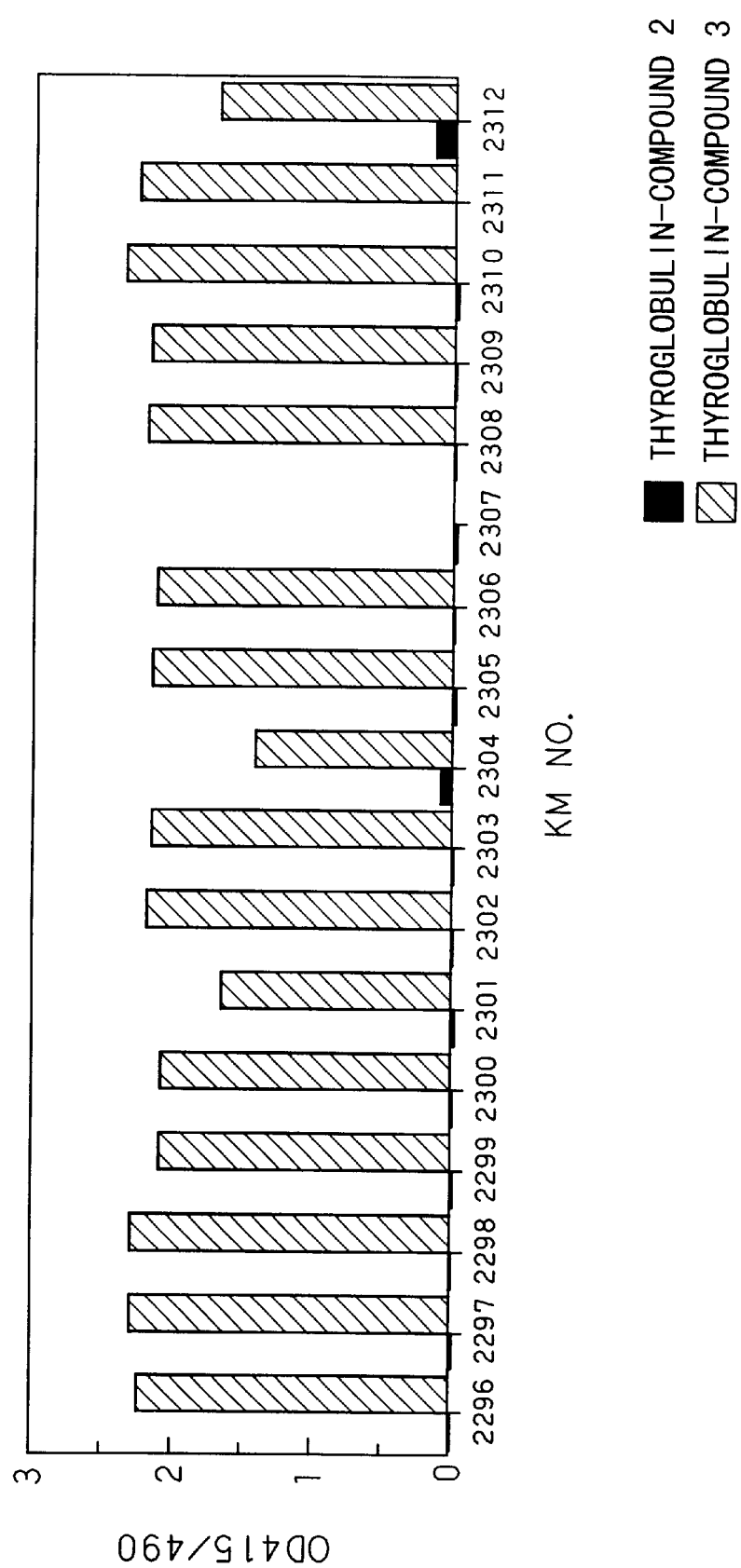
FIG. 3 is a graph showing the results of reactivity for Compounds 2 and 3 of the monoclonal antibodies of the present invention obtained using Compound 3 as an antigen, by enzyme-linked immunosorbent assay.

As shown in FIG. 1, the anti-hTERT monoclonal antibodies (KM2294 and KM2295) obtained using Compound 2 (SEQ ID NO: 1) reacted specifically with Compound 2. As shown in FIG. 2, the anti-hTERT monoclonal antibodies (KM2277 to KM2284) obtained using Compound 1 (SEQ ID NO: 2) reacted specifically with Compound 1. As shown in FIG. 3, the monoclonal antibodies (KM2296 to KM2312) obtained using Compound 3 (SEQ ID NO: 3) in the antigen reacted specifically with Compound 3.

(9) Western Blotting

Detection of hTERT protein within cells by Western blotting was studied using the anti-hTERT monoclonal antibodies selected in Example 1 (6).

Figure 4:
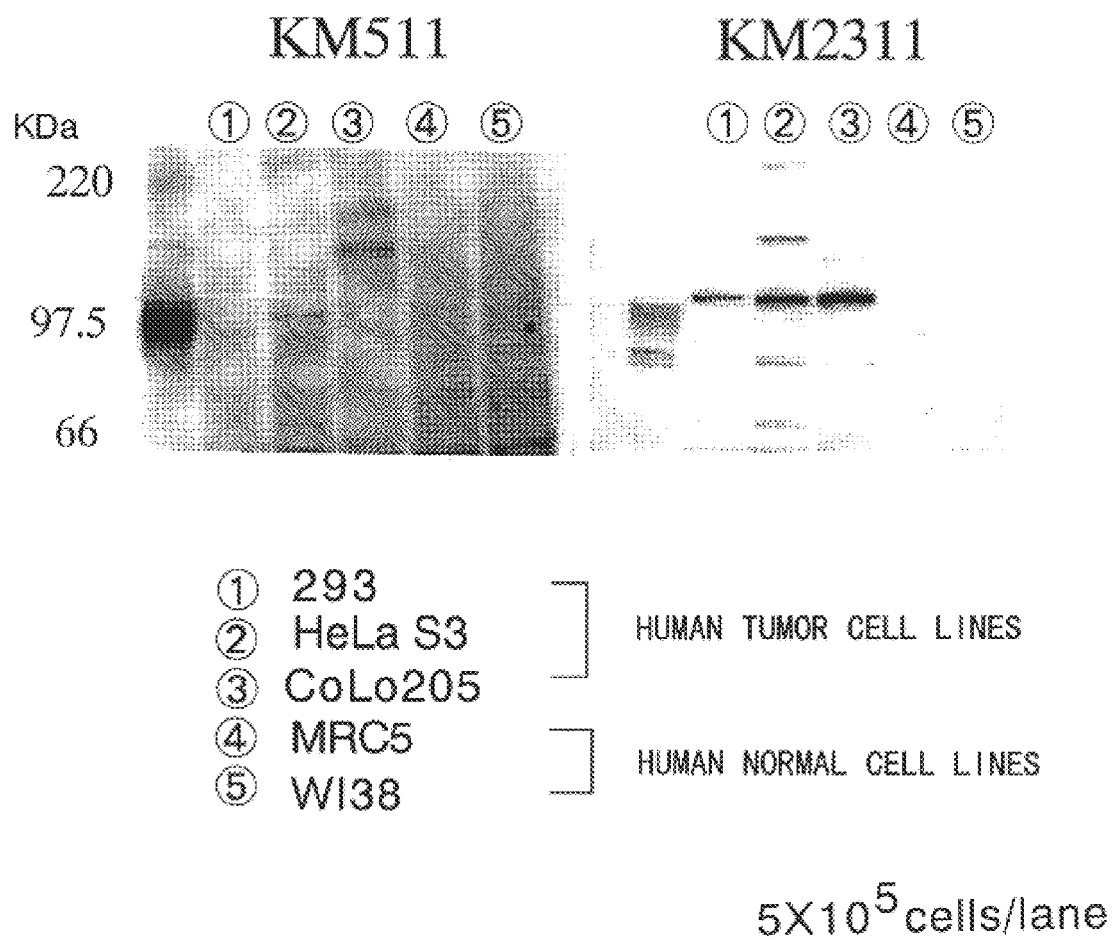
FIG. 4 is a photograph showing the results of the detection of hTERT protein present within cells by Western blotting using the monoclonal antibodies of the present invention.

Five types of cells, human renal transformant 293 (ATCC CRL1537), human cervical cancer cell line HeLaS3 (ATCC CCL-2.2), human colon cancer cell line CoLo205 cell (ATCC CRL-225), normal human lung cells MRC5 (ATCC CCL-171), and normal human lung cells WI-38 cell (ATCC CCL-75), were used. Cells of these lines were floated in a tripsin and EDTA solution mixture (Sankou Junyaku) and washed in PBS. 1 ml of buffer for cytolysis (50 mM Tris-HCL, pH 7.2, 1% TritonX, 150 mM NaCl, 2 mM $MgCl_2$, 2 mM $CaCl_2$, 0.1% $NaN_3$, 50 mM iodoacetamide, 50 mM N-ethylmaleidmide, 1 mg/ml leupepcin, and 0.1 mM dithiothreitol) was added to $5\times10^7$ cells, and allowed to stand to for 2 hours at 4° C., and then centriftiged. After fractionation of the obtained supernatant by SDS-electrophoresis with $10^5$ cells per lane (Antibodies—A Laboratory Manual, Cold Spring Harbor Laboratory, 1988), blotting to a PVDF membrane was carried out. After blocking with BSA-PBS, the culture supernatant of the anti-hTERT monoclonal antibodies was allowed to react for 2 hours at room temperature. After washing wells with PBS-Tween, a reaction with anti-mouse immunoglobulin antibody (manufactured by Dako. Co.) labeled with peroxidase as the second antibody was carried out for 1 hour at room temperature. After washing well with PBS-Tween, detection was carried out using an ECL detection kit (Amersham Co.), and sensitized on X-ray film. The results are shown in FIG. 4. In FIG. 4, Lane 1 shows the results for the 293 cytolysis solution, Lane 2 shows the results for the HeLaS3 cytolysis solution, Lane 3 shows the results for the CoLo205 cell cytolysis solution, Lane 4 shows the results for the MRC 5 cytolysis solution, and Lane 5 shows the results for the WI-38 cell cytolysis solution.

As shown in FIG. 4, using KM2311 (the anti-hTERT monoclonal antibodies obtained by means of Compound 3), bands were detected in the cytolysis solution of 293 cells, HeLaS3 cells, and CoLo205 cells, in the vicinity of 130 KDa which corresponds to the molecular weight of hTERT. In addition, in the cytolysis solutions of the MRC5 cells and WI-38, which are normal cells, a specific band was not detected. With regard to monoclonal antibody KM511 which does not react with hTERT [Agric. Biol. Chem., 53(4), 1095 (1989)], none reacted specifically in the vicinity of 130 KDa band.

The above results show that KM2311 is able to detect hTERT protein within cells by Western blotting and that it can be used in the diagnosis of diseases, such as cancer, in which telomerase is involved.

3(10) Dot Blotting

Detection of hTERT protein within cells by dot blotting was studied using anti-hTERT monoclonal antibodies. As the anti-hTERT monoclonal antibodies, the culture supernatant of KM2311 detected hTERT protein in Example 1 (7) was used.

Figure 5:
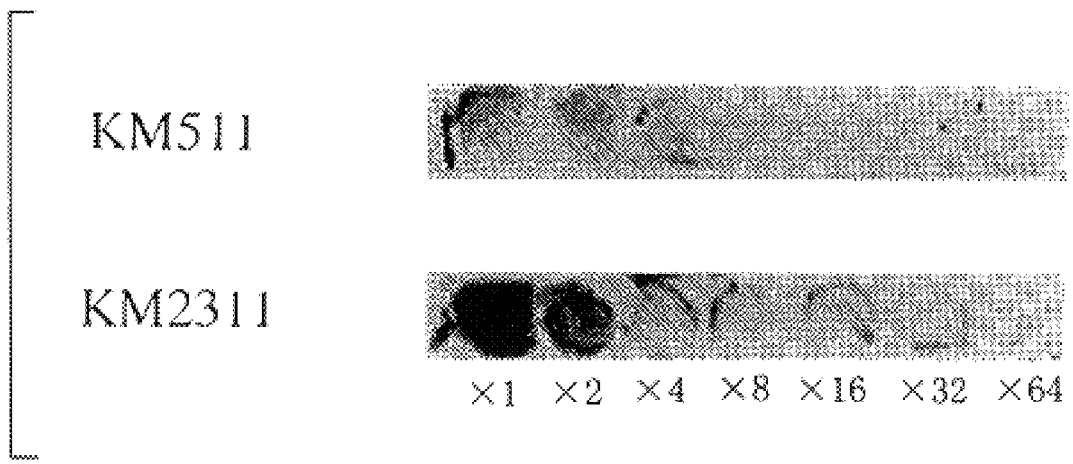
FIG. 5 is a photograph showing the results of the detection of hTERT protein present within cells by dot blotting using the monoclonal antibodies of the present invention.

Cytolysis solution of human renal transformant 293 cells prepared in Example 1 (7), in a concentration of $2.5\times10^5$ cells/5 μl was diluted by 2, 4, 8, 16, 32 and 64 times with cytolysis buffer, and then each of these was dotted onto a nitrocellulose membrane in an amount of 5 μl per spot. After drying, and after blocking with BSA-PBS, they were reacted with KM2311 culture supernatant for 2 hours at room temperature at undiluted solution. After washing well with PBS-Tween, a reaction with anti-mouse immunoglobulin antibodies labeled with peroxidase as the second antibody was carried out for 1 hour at room temperature. After washing well with PBS-Tween, detection was carried out using an ECL-detection kit (Amersham CO.) and sensitized on an X-ray film. The results are shown in FIG. 5. In FIG. 5, the upper column is the result of KM511 and the lower column is the result of KM2311. In FIG. 5, the results of the reaction with the nitrocellulose membrane on which the cytolysis solution of human renal transformant 293 was spotted, from the left, as undiluted solution, 2, 4, 8, 16, 32, and 64 times dilutions, are shown.

As shown in FIG. 5, KM2311 is able to detect hTERT protein within cells by dot blotting and that it can be used in the diagnosis of diseases, such as cancer, in which telomerase is involved.

(11) Immunocyte Staining

Detection of hTERT protein within cells by means of immunocyte staining was studied using the anti-hTERT monoclonal antibodies selected in Example 1 (6).

A total of five cell lines, human renal transformant 293 (ATCC CRL1537), human cervical cancer cell line HeLaS3 (ATCC CCL-2.2), human colon cancer cell line CoLo205 cell (ATCC CRL-225), normal human lung cells MRC5 (ATCC CCL-171), and normal human lung cells WI-38 cell (ATCC CCL-75), were used. Cells of these lines were floated in a tripsin and EDTA solution mixture and washed in PBS. Then, in order to increase penetrability of the cell membrane by antibodies, they were treated for 10 minutes at 4° C. in 100% methanol (chilled on ice). After washing with PBS, blocking was carried out for 30 minutes at room temperature with 10 μg/ml of human immunoglobulin (Cappel Co.). After adding ×10⁵ cells per tube, centrifugation was conducted and the supernatant removed, and culture supernatant of the anti-hTERT monoclonal antibody added and allowed to react for 30 minutes at room temperature. After washing in PBS, 100 μl of anti-mouse immunoglobulin antibody (specific for mouse immunoglobulin, Wako Junyaku) was added per tube, and allowed to reacted with shielding for 30 minutes at 4° C. After washing well with PBS, analysis using a cell analyzer (Coulter Co; EPICS XL system II) was carried out.

Figure 6:
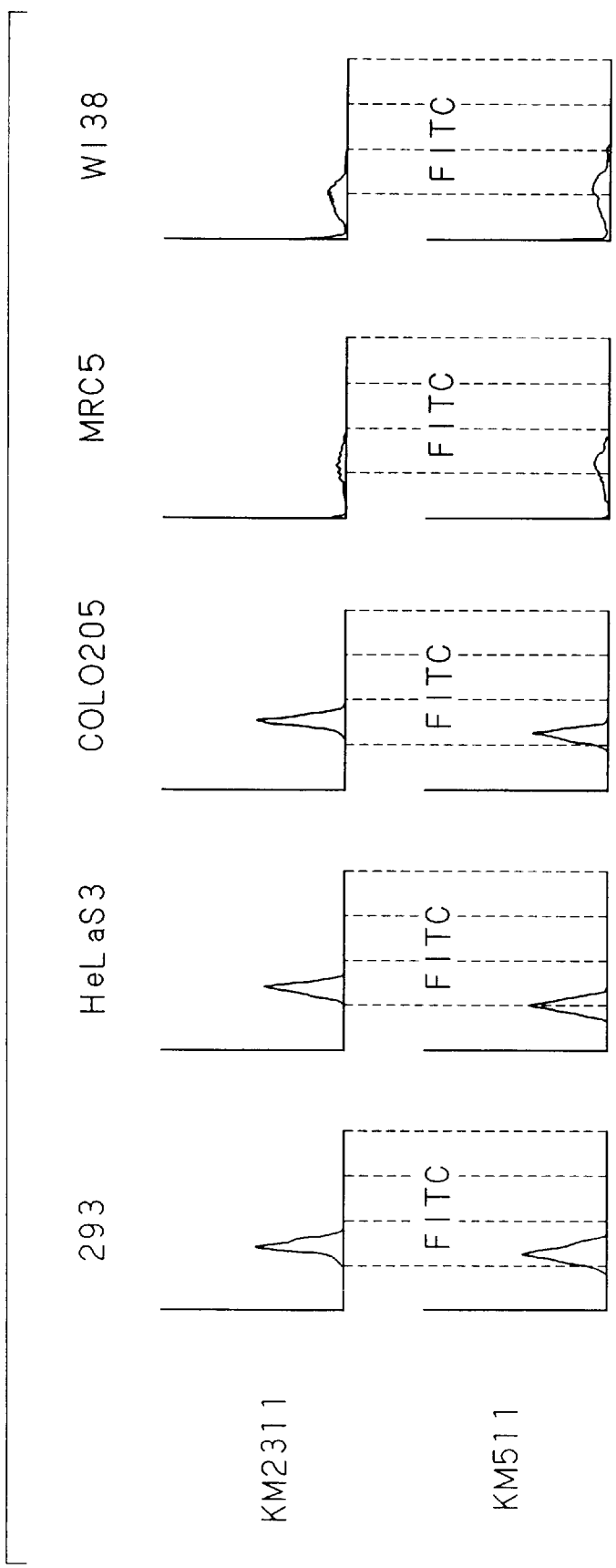
FIG. 6 is a chart showing the results of the detection of hTERT protein present within cells by cytological staining using the monoclonal antibodies of the present invention.

FIG. 6 shows charts of the cell analysis, and the results with regard to each of the 293 cells (left column), HeLaS3 cells (center column), CoLo205 cells, MARC5 cells, and W138 cells was shown in case of the addition of KM2311, KM511, and BSA.

The peak shift in FIG. 6 indicates that KM2311 reacts with 293 cells, HeLaS3 cells, and CoLo205 cells. In addition, reactivity of KM2311 with MRC5 cells or W138 cells, which are normal cells, is not recognized. Monoclonal antibodies other than KM2311 did not show specific reactivity to cancer cell lines.

Consequently, KM2311 is able to detect hTERT protein within cells by means of cytological staining and shows that it can be used in the diagnosis of various diseases, such as cancer, in which telomerase is involved.

EXAMPLE 2

Preparation of the Anti-hTERT Monoclonal Antibody (2)

(1) Production of an Expression Plasmid for the Human Telomerase Catalytic Subunit in *Escherichia coli*

An expression plasmid for the fusion protein of a partial fragment of human telomerase catalytic subunit (hTERT) with glutathione-S-transferase (hereinafter referred to as GST) in *Escherichia coli* was constructed as follows.

First, synthetic DNA primers were produced using a gene portion corresponding to 549 to 831 amino acid residues (SEQ ID NO: 6) [Science, 277, 955 (1997)] of hTERT which have total 1132 amino acid residues, as a probe, respectively. SEQ ID NO: 4 is a nucleotide sequence in which a recognition sequence by BamHI is combined to 5' terminal of a nucleotide sequence corresponding to 439 to 555 amino acid residues. SEQ ID NO: 5 is a nucleotide sequence in which a recognition sequence by EcoRI is combined to the 5' terminal of a nucleotide sequence corresponding to 825 to 831 amino acid residues. The DNA was amplified by means of PCR using these synthetic DNA primers. The reaction conditions were as follows: after allowing to stand for 1 minute at 94° C., repeating 25 cycles consisting of 20 seconds at 94° C., 30 seconds at 55° C., and 2 minutes at 72° C.; then, allowing to stand 72° C. for 10 minutes; and shifting to 4° C. As thermal resistant DNA polymerase, LA Taq DNA polymerase manufactured by Takara Co. was used. The obtained PCT product was digested with restriction enzymes BamHI and EcoRI, the sample was subject to electrophoresis in agarose gel, the DNA band was cut out, and thereby the DNA was extracted and purified. The purified fragment was inserted into BamHI-EcoRI site in pGEX-2TK (manufactured by Pharmacia Co.), in which the DNA coding for GTS was incorporated, and the obtained plasmid was named phTERT.

(2) Preparation of a Recombinant Fusion Protein of the Human Telomerase Catalytic Subunit

*Escherichia coli* strain DH5 α in which the expression plasmid phTERT was introduced as described in Example 2(1) was cultured over night in 450 ml of LB medium, and the whole culture was inoculated into 18 L of LB medium (containing 0.1 mg/ml ampicillin) and cultured at 37° C. while shaking. When the OD600 value reached a value of 0.2, isopropyl-β-D-thiogalactoside was added so that final content thereof became 2 mM, and the shaking culture was continued for 3 additional hours at 37° C. By the centrifugation of the culture at 4° C. at 8,000 rpm for 1 hour, the cells were collected, suspended in 100 ml of PBS, and sonicated. Then the mixture was centirufuged at 4° C. at 8,000 rpm for 1 hour, and the precipitation fraction was suspended in 100 ml of PBS/1% Tween 20. Then, the centrifugation and the suspending as above described were repeated 5 times, the final precipitation fraction was collected as an inclusion body fraction, and used as an antigen in the preparation of antibody as follows.

(3) Preparation of the Monoclonal Antibody Using Fusion Protein of the Human Telomerase Catalytic Subunit Expressed in *Escherichia coli*

The GST-hTERT fragment as prepared above was purified by SDS-PAGE. SDS-PBS was added to the inclusion body fraction so that the final concentration of SDS became 0.5%, and the mixture was heated for 5 minutes at 100° C., and solubilized. The inclusion body fraction was fractionated by electrophoresis (SDS-PAGE) using polyacrylamide gel of 2 mm thickness. The gel was stained by 1% Coomassie Brilliant Blue solution, and decolorized with water. The band corresponding to the molecular weight of the GST-hTERT fragment was cut out, and extracted over night at 4° C. in 0.1% SDS-PBS. The extract was filtered through a glass filter, and the filtrate containing GST-hTERT fragment was collected for use as antigen.

The obtained GST-hTERT fragment which was expressed in *Escherichia coli* and purified by SDS-PAGE as above was administered at dosage of 50 μg/body three times to five-week aged female mouse, the first administration being together with 2 mg aluminum gel and $1 \times 10^9$ cells of pertussis vaccine. After that, the hybridomas were prepared based on the method described in Examples 1(3) to (7), provided that the GST-hTERT fragment expressed in *Escherichia coli* was used as an antigen for assay in the enzyme-linked immunosorbent assay.

As a result, KM2582, KM2590, KM2591, and KM2604, which specifically reacted with GST-hTERT fragment, were obtained. The subclasses of the antibodies, which were determined by the binding ELISA shown in section (4), were IgG2b class for KM2582, KM2590, and KM2591; and IgG2a class for KM2604.

(4) The Binding ELISA

Figure 7:
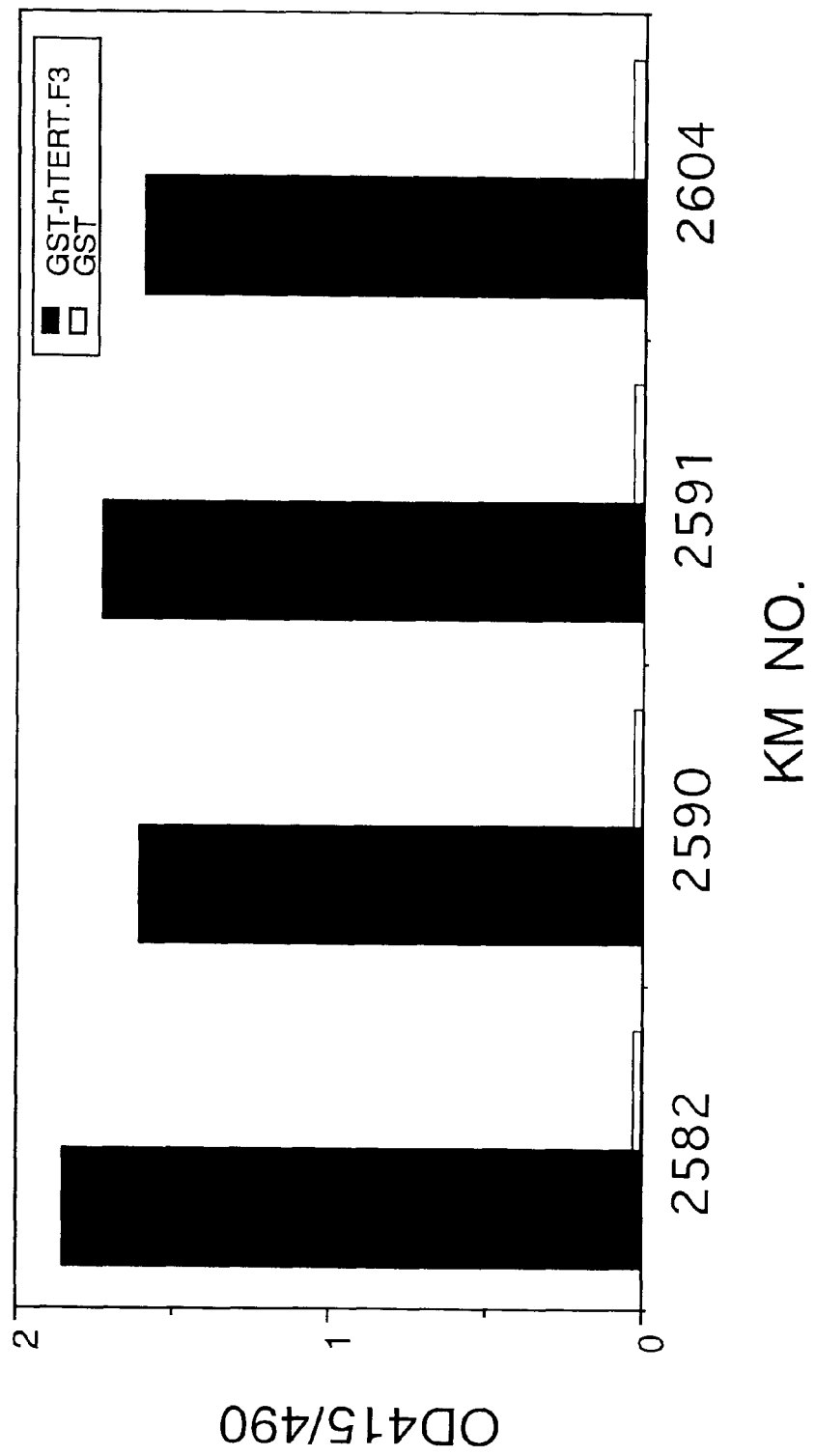
FIG. 7 is a graph showing the results of reactivity of KM2582, KM2590, and KM2591, KM2604, which specifically react with GST-hTERT.F3, by enzyme-linked immunosorbent assay.

GST-hTERT.F3, which was expressed in *Escherichia coli* and purified by SDS-PAGE, was used as the antigen for the assay. As the control antigen, GST was used. The preparation of GST was carried out in a similar way as the above-mentioned Examples 2 (1) to (3). Thereafter, the enzyme-linked immunosorbent assay described in Example 1(4) was carried out. The results are shown in FIG. 7. All of KM 2582, KM 2590, KM 2591, and KM2604 showed the specific reactivities to GST-hTERT.F3, which was expressed in *Escherichia coli* and purified by SDS-PAGE.

(5) Western Blotting

The detection of the hTERT protein in cells by Western blotting was studied using the anti-hTERT monoclonal antibodies selected in Example 2(3).

For cell lines, human renal transformant 293 (ATCC CRL1537) and normal human lung cells WI-38 cell (ATCC CCL-75) were used. For the second antibody, anti-rat imunoglobulin (manufactured by Dako. Co.) labeled with peroxidase, which reacts specifically to rat imunoglobulin, was used. The procedures according to the method described in Example 1 (9) were followed.

Figure 8:
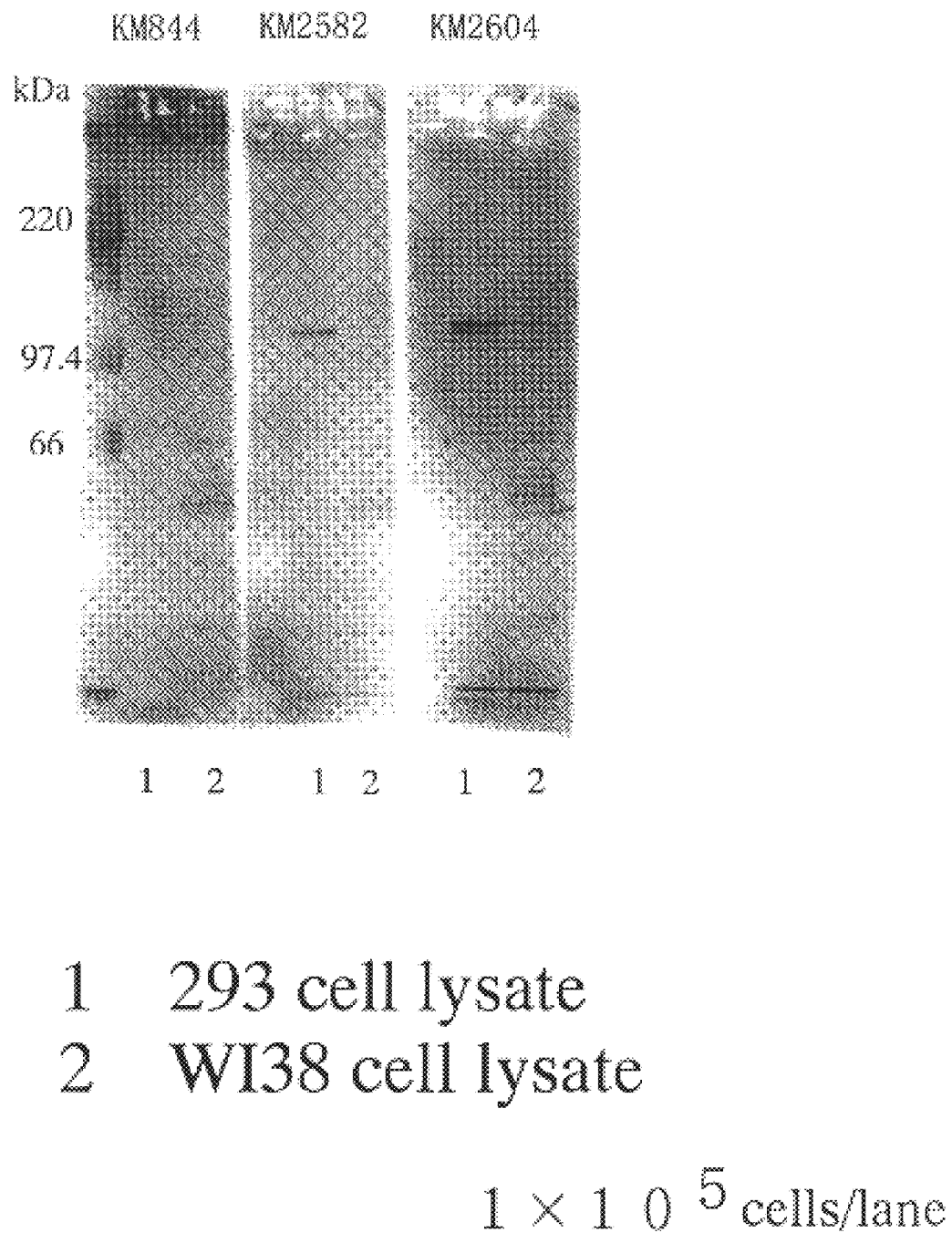
FIG. 8 is a photograph showing the results of the detection of hTERT protein present within cells by Western blotting using the monoclonal antibodies of the present invention.

The results are shown in FIG. 8. In FIG. 8, Lane 1 shows the results for the 293 cytolysis solution, and Lane 2 shows the results for the WI38 cytolysis solution.

As shown in FIG. 8, using KM2582 and KM2604, bands were detected in the cytolysis solution of 293 cells, in the vicinity of 130 KDa which corresponds to the molecular weight of hTERT. In the cytolysis solutions of WI-38, which are normal cells, a specific band was not detected. The KM844, which is the IgG type monoclonal antibody for DU189 and which was used as a control antibody, did not react with any cells.

(6) Immunocyte Staining

Detection of hTERT protein within cells by immunocyte staining was studied using the anti-hTERT monoclonal antibodies selected in Example 2 (3).

For cell lines, human renal transformant 293 (ATCC CRL1537) and normal human lung cells WI-38 cell (ATCC CCL-75) were used. For the second antibody, anti-rat imunoglobulin (manufactured by Dako. Co.) labeled with FITC, which reacts specifically to rat imunoglobulin, was used. The procedures according to the method described in Example 1 (11) were followed.

The results are shown in FIG. 9. As shown in FIG. 9, KM2582 and KM2604 reacted with 293 cells, and did not react with the WI-38 cell, which is a normal cell. The KM844, which is the IgG type monoclonal antibody for DU189 and which was used as a control antibody, did not react with any cells.

(7) Construction of Quantitating System of hTERT Protein

In order to construct a determination system for hTERT protein, the following experiments were carried out.

First, the insect cell nucleus extract of the cells expressing the hTERT protein and the insect cell nucleus extract of the cells expressing only a vector were prepared according to the following method. The hTERT gene described in Example 2 (1) was inserted at the EcoRI site in pVL1392 (Pharmingen Co.), and thereby the transfer vector pVL-hTERT was constructed. This vector was introduced into St21 cells together with Baculo Gold (Pharmingen Co.). After culturing for 4 days at 27° C., a virus vector expressing hTERT was obtained from the culture supernatant. In addition, PVL1392 having no hTERT gene and Baculo Gold were introduced into Sf2l, and the obtained virus vector was used for the negative control experiment.

Sf21 cells were infected with the above-described virus vector at three plaque forming units per cell. After culturing for 3 days at 27° C., cells were collected and suspended at a concentration of $5 \times 10^6$ cells/ml in 1×CHAPS buffer (10 mM Tris/HCl (pH7.5), 1 mM $MgCl_2$, 1 mM EGTA, 5 mM β-mercaptoethanol, 0.5% (w/v) CHAPS, and 10% glycerol). After allowing to stand on ice for 30 minutes, the nucleus fraction was collected as precipitation by centrifuging at 4° C. at 12,000 rpm for 20 minutes.

The precipitation was suspended in the same volume of KCl solved buffer (50 mM Tris/HCl (pH 7.5), 420 mM KCl, 5 mM $MgCl_2$, 0.1 mM EDTA, 6 mM dithiothreitol, 0.5% (w/v) CHAPS, 20% glycerol, and 10% sucrose), and the cell nucleus extract containing human telomerase catalytic subunit was obtained with ultrasonic treatment.

Next, the anti-hTERT monoclonal antibody KM2311 which was obtained in Examples 1 (1) to (7) was labeled with biotin as follows. Purified KM 2311 antibody was diluted to 1 mg/ml with PBS, and the 1/4 volume of 0.5M carbonate buffer (pH9.2) was added to the antibody solution. Furthermore, NHS-Lc-Biotin (solved in dimethylformamide at a concentration of 1 mg/ml; manufactured by Pierce Co.) was added dropwise with stirring to the antibody solution. After the reaction with stirring for 3 hours at room temperature, and dialysis in PBS over night, KM2311 labeled with biotin was obtained and used thereafter.

To a 96 well EIA plate (Griener Co.), 50 μl of the 4 μg/ml anti-rat immunoglobulin antibody (mouse antibody absorption finished; manufactured by Cartag Co.) was added to each well and allowed to be adsorbed onto the plate by allowing to stand over night at 4° C. After washing, 100 μl of 1% BSA-PBS was added to each well, reacted for 1 hour at room temperature, and the remaining active groups blocked. The 1% BSA-PBS in the wells was discarded, each of undiluted culture supernatant of the hybridomas KM2590 and KM2591 was added each well and allowed to read over night at 4° C. After washing the wells with PBS, a series of five-fold dilution was repeated seven times with respect to each of insect cell nucleus extracts of cells expressing the hTERT protein and the insect cell nucleus extracts of cells expressing only a vector, and each of the diluted extracts was added to each well, and allowed to react over night at 4° C. After washing the wells with tween-PBS, 50 μl of the above-mentioned KM2311 labeled with biotin (diluted in BSA-PBS containing 1% normal rat serum to 1 μg/ml) was added to each well, and allowed to react for 2 hours at room temperature. Then after washing the wells with tween-PBS, 50 μl of avidin labeled with peroxidase (Vector Co.) was added to each well, and allowed to react for 1 hours at room temperature. Then, after washing the wells with tween-PBS, the color was developed using ABTS matrix liquid [2.2-adinobis (3-ethylbenzothiazole-6-sulfonic acid) ammonium] and OD415 nm absorbance measured using a plate reader (E-max; manufactured by WAKO JUNYAKU).

Figure 10:
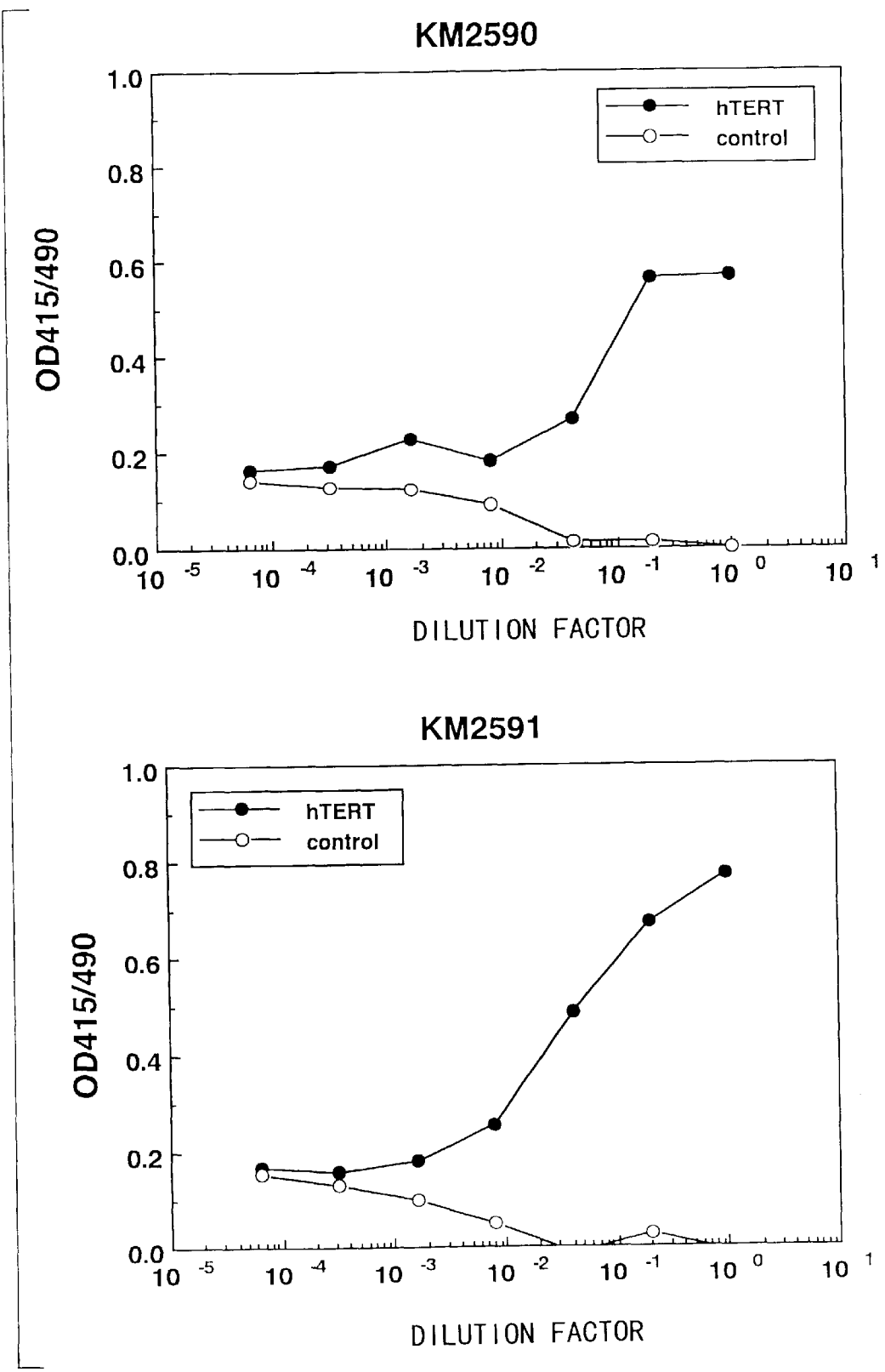
FIG. 10 is a graph showing the results of the detection of hTERT protein present within cells by sandwich ELISA method using the monoclonal antibodies of the present invention.

As a result shown in FIG. 10, the hTERT protein can be detected concentration-dependently and specifically by the sandwich ELISA method using KM2590 or KM2591 and biotinized KM2311. Therefore, this method in which hTERT protein having a known concentration is used as the standard sample, makes it possible to detect hTERT, and is useful in the diagnosis of diseases, such as cancer, in which telomerase is involved.

(8) Immune Precipitation

The immune precipitation was studied using the insect cell nucleus extract of the cell expressing hTERT protein and the insect cell nucleus extract of the cell expressing only a vector, prepared in Example 2 (7).

To a 96 well EIA plate (Griener Co.), 100 μl of anti-rat immunoglobulin (manufactured by Cartag Co.) were added to each well and allowed to stand over night at 4° C. to be coated on the plate. Then, 200 μl of BSA-PBS were added to each well, allowed to stand for 1 hour at room temperature, and the remaining active groups were blocked. Then, the BSA-PBS in the wells was discarded, 100 μl of undiluted culture supernatant of the control antibody KM844, the hybridoma KM2590, or KM2591 were added respectively to each well and allowed to react for 2 hours at room temperature. After washing thoroughly with PBS, 100 μl of the cell extract was added to each well and allowed to react over night at 4° C. After washing thoroughly in wells with PBS-tween, 20 μl of sample buffer (five fold concentration) for SDS-PAGE was added to each well, the plate was shaken for 2 hours, and all contents were poured into tubes. The collected samples were diluted five times PBS, and according to a usual method, SDA-PAGE was performed, followed by Western blotting. Then, the antibody staining was carried out using the anti-hTERT monoclonal antibody KM2311 obtained in Example 1.

The results are shown in Table 2. As shown in Table 2, the protein having a molecular weight of 130 kDa, which is detected by KM2311, was precipitated only by KM2591. In addition, the precipitate protein was not detected using the control insect cell nucleus extract as an antigen.

TABLE 2

| Antigen Antibody | Nucleus Extract of Insect Cell Expressing hTERT | | | Nucleus Extract of Control Insect Cell | | |
|---|---|---|---|---|---|---|
| body | KM844 | KM2590 | KM2591 | KM844 | KM2590 | KM2591 |
| Results | − | − | + | − | − | − |

Industrial Applicability

According to the present invention, anti-hTERT monoclonal antibodies are provided which react specifically with hTERT and which detect specifically hTERT protein by Western blotting, immunocyte staining and dot blotting.

In these methods, anti-hTERT monoclonal antibodies which detect hTERT protein specifically and diagnosis kits using said anti-hTERT monoclonal antibody enable highly sensitive detection in the diagnosis of diseases in which telomerase is involved.

What is claimed is:

1. A monoclonal antibody, wherein said monoclonal antibody reacts specifically with the amino acid sequence of the human telomerase catalytic subunit, the sequence being designated as one of SEQ ID NOs: 1 and 3.

2. A monoclonal antibody according to claim 1, wherein said monoclonal antibody is obtainable by immunizing an animal with a partial peptide of the human telomerase catalytic subunit, the partial peptide having an amino acid sequence designated as one of SEQ ID NOs: 1 and 3.

3. A monoclonal antibody, wherein said monoclonal antibody is selected from the group consisting of monoclonal antibodies KM2311, KM2582, KM2590, KM2591, and KM2604.

4. (Amended) An antibody characterized in that said antibody according to one of claims 1 and 3 is bound to a radioactive isotope, a protein, or a low molecular agent by chemical or genetic engineering method.

5. A diagnosis agent for diseases wherein telomerase is involved using the monoclonal antibody according to one of claims 1 and 3.

6. A therapeutic agent for diseases wherein telomerase is involved using the monoclonal antibody according to one of claims 1 and 3.

7. A hybridoma which produces the monoclonal antibody wherein said hybridoma is selected from the group consisting of KM2311 (FERM-BP3603), KM2582 (FERM BP-6663), KM2590 (FERM 6683), KM2591 (FERM BP-6684), and KM2604 (FERM BP-6664).

8. A human chimeric antibody comprising an antibody heavy chain (H chain) variable region (V region) and an antibody light chain (L chain) V region of the monoclonal antibody, and H chain constant region (C region) and L chain C region of a human antibody, wherein amino acid sequences of said H chain V region and L chain V region have the same amino acid sequences as amino acid sequences of an H chain V region and an L chain V region of a monoclonal antibody selected from the group consisting of monoclonal antibodies KM2311, KM2582, KM2590, KM2591, and KM2604.

9. A human chimeric antibody according to claim 8, wherein amino acid sequences of said H chain V region and L chain V region have the same amino acid sequences as amino acid sequences of an H chain V region and an L chain V region of a monoclonal antibody selected from the group consisting of monoclonal antibodies KM 2311, KM2582, KM2590, KM2591, and KM2604.

10. A CDR grafted antibody comprising V region complementary determining regions of H chain and L chain of the monoclonal antibody, and C region and V region framework regions of an H chain and an L chain of a human antibody, wherein amino acid sequences of said complementary determining regions of the H chain V region and L chain V region have the same amino acid sequences as amino acid sequence of complementary determining regions of an H chain V region and L chain V region of a monoclonal antibody which is selected from the group consisting of monoclonal antibodies KM2311, KM2582, KM2590 KM2591, and KM2604.

11. A disulfide stabilized antibody comprising H chain V region and L chain V region of monoclonal antibody, wherein amino acid sequences of an H chain V region and an L chain V region of said disulfide stabilized antibody have the same amino acid sequence as amino acid sequences of an H chain V region and an L chain V region of a monoclonal antibody which is selected from the group consisting of monoclonal antibodies KM2311, KM2582, KM2590, KM2591, and KM2604.

12. A disulfide stabilized antibody comprising H chain V region and L chain V region of monoclonal antibody, wherein amino acid sequences of an H chain V region and an L chain V region of said disulfide stabilized antibody have the same amino acid sequence as amino acid sequences of complementary determining regions of an H chain V region and an L chain V region of a monoclonal antibody which is selected from the group consisting of monoclonal antibodies KM 2311, KM2582, KM2590, KM2591, and KM2604.

* * * * *